(12) United States Patent
Krieg et al.

(10) Patent No.: US 6,218,371 B1
(45) Date of Patent: Apr. 17, 2001

(54) METHODS AND PRODUCTS FOR STIMULATING THE IMMUNE SYSTEM USING IMMUNOTHERAPEUTIC OLIGONUCLEOTIDES AND CYTOKINES

(75) Inventors: Arthur M. Krieg; George Weiner, both of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/286,098

(22) Filed: Apr. 2, 1999

Related U.S. Application Data
(60) Provisional application No. 60/080,729, filed on Apr. 3, 1998.

(51) Int. Cl.[7] .......................... A01N 43/04; A01N 37/18; A61K 39/00; C12Q 1/68; C07H 21/02
(52) U.S. Cl. ...................... 514/44; 514/2; 424/180.1; 424/185.1; 435/6; 435/91.1; 435/455; 536/23.1
(58) Field of Search .................. 424/180.1, 184.1, 424/185.1, 192.1, 193.1, 278.1; 435/91.1, 91.5, 325, 455, 6; 514/44; 530/300, 350, 351; 536/23.1, 23.4, 23.5, 23.51, 23.52, 25.3

(56) References Cited

U.S. PATENT DOCUMENTS

| | | | |
|---|---|---|---|
| 3,906,092 | 9/1975 | Hilleman et al. | 424/209.1 |
| 5,212,295 | 5/1993 | Cook | 536/26.7 |

(List continued on next page.)

FOREIGN PATENT DOCUMENTS

| | | |
|---|---|---|
| 0468520 A3 | 1/1992 | (EP) . |
| 0302758 B1 | 3/1994 | (EP) . |
| WO 91/12811 | 9/1991 | (WO) . |
| WO 92/03456 | 3/1992 | (WO) . |

(List continued on next page.)

OTHER PUBLICATIONS

Adya N et al., Expansion of CREB's DNA recognition specificity by Tax results from interaction with Ala–Ala–Arg at positions 282–284 near the conserved DNA–binding domain of CREB. *Proc Natl Acad Sci USA* 91(12):5642–6, Jun. 7, 1994.

Angier, N., Microbe DNA Seen as Alien By Immune System, *New York Times,* Apr. 11, 1995.

Azad RF et al., Antiviral Activity of a Phosphorothioate Oligonucleotide Complementary to RNA of the Human Cytomegalovirus Major Immediate–Early Region. *Antimicrobial Agents and Chemotherapy,* 37:1945–1954, Sep., 1993.

(List continued on next page.)

*Primary Examiner*—Remy Yucel
*Assistant Examiner*—Jane Zara
(74) *Attorney, Agent, or Firm*—Wolf, Greenfield & Sacks, P.C.

(57) ABSTRACT

The present invention relates to synergistic combinations of immunostimulatory CpG oligonucleotides and immunopotentiating cytokines. In particular, the invention relates to methods of stimulating an immune response using the synergistic combination of compounds and products related thereto.

23 Claims, 9 Drawing Sheets

CpG ODN ENHANCES THE PROTECTIVE EFFECT OF IMMUNIZATION WITH Id/GM-CSF

U.S. PATENT DOCUMENTS

| | | | |
|---|---|---|---|
| 5,248,670 | 9/1993 | Draper et al. | 514/44 |
| 5,506,212 | 4/1996 | Hoke et al. | 514/44 |
| 5,521,302 | 5/1996 | Cook | 536/25.31 |
| 5,585,479 | 12/1996 | Hoke et al. | 536/24.5 |
| 5,599,797 | 2/1997 | Cook et al. | 514/44 |
| 5,663,153 | 9/1997 | Hutcherson et al. | 514/44 |
| 5,723,335 | 3/1998 | Hutcherson et al. | 435/375 |
| 5,750,674 | 5/1998 | Iyer et al. | 536/26.7 |
| 5,780,448 * | 7/1998 | Davis et al. | 514/44 |
| 5,786,189 | 7/1998 | Locht et al. | 424/200.1 |
| 5,837,856 | 11/1998 | Arnold, Jr. et al. | 536/24.5 |
| 5,849,719 | 12/1998 | Carson et al. | 514/44 |
| 5,856,465 | 1/1999 | Stec et al. | 536/25.3 |
| 5,869,057 * | 2/1999 | Rock et al. | 424/192.1 |
| 5,883,237 | 3/1999 | Stec et al. | 536/23.1 |
| 5,904,920 * | 5/1999 | Dranoff et al. | 424/93.21 |
| 5,908,845 | 6/1999 | Segev | 514/261 |

FOREIGN PATENT DOCUMENTS

| | | |
|---|---|---|
| WO 92/18522 | 10/1992 | (WO) . |
| WO 92/21353 | 12/1992 | (WO) . |
| WO 94/19945 | 9/1994 | (WO) . |
| WO 95/05853 | 3/1995 | (WO) . |
| WO 95/26204 | 10/1995 | (WO) . |
| WO 96/02555A1 | 2/1996 | (WO) . |
| WO 96/19572 | 6/1996 | (WO) . |
| WO 96/35782 | 11/1996 | (WO) . |
| WO 96/39154 | 12/1996 | (WO) . |
| WO 97/28259 | 8/1997 | (WO) . |
| WO 98/14210 | 4/1998 | (WO) . |
| 9816247 * | 4/1998 | (WO) . |
| WO 98/18810 | 5/1998 | (WO) . |
| WO 98/37919 | 9/1998 | (WO) . |
| WO 98/40100 | 9/1998 | (WO) . |
| WO 98/52581 | 11/1998 | (WO) . |
| WO 00/06588 | 2/1999 | (WO) . |

OTHER PUBLICATIONS

Azuma, Biochemical and Immunological Studies on Cellular Components of Tubercle Bacilli, *Kekkaku*, vol. 69, 9:45–55, 1992.

Ballas ZK et al., Induction of NK activity in murine and human cells by CpG motifs in oligodeoxynucleotides and bacterial DNA. *J Immunol* 157(5):1840–5, 1996.

Bayever, E., Systemic Administration of a Phosphorothioate Oligonucleotide with a Sequence Complementary to p53 for Acute Myelogenous leukemia and Myelodysplastic Syndrome: Initial Results of a Phase I Trial, *Antisense Res. & Dev.* (1993), 3:383–390.

Bennett RM et al., DNA binding to human leukocytes. Evidence for a receptor–mediated association, internalization, and degradation of DNA. *J Clin Invest* 76(6):2182–90, 1985.

Berg DJ et al., Interleukin–10 is a central regulator of the response to LPS in murine models of endotoxic shock and the Shwartzman reaction but not endotoxin tolerance. *J Clin Invest* 96(5):2339–47, 1995.

Blanchard DK et al., Interferon–gamma induction by lipopolysaccharide: dependence on interleukin 2 and macrophages. *J Immunol* 136(3):963–70, 1986.

Blaxter et al., Genes expressed in Brugia malayi infective third stage larvae. *Molecular and Biochemical Parasitology*, 77:77–93. 1996.

Boggs RT et al., Characterization and modulation of immune stimulation by modifed oligonucleotides. *Antisense Nucleic Acid Drug Dev* 7(5):461–71, Oct. 1997.

Branda RF et al., Amplification of antibody production by phosphorothioate oligodeoxynucleotides. *J. Lab Clin Med* 128(3):329–38, Sep. 1996.

Branda et al., Immune Stimulation by an Antisense Oligomer Complementary to the rev gene of HIV–1. *Biochemical Pharmacology*, vol. 45, 10:2037–2043, 1993.

Briskin M et al., Lipopolysaccharide–unresponsive mutant pre–B–cell lines blocked in NF–kappa B activation. *Mol Cell Biol* 10(1):422–5, Jan. 1990.

Chace, J. et al., Regulation of Differentiation in CD5+ and Conventional B Cells, *Clinical Immunology and Immunopathology*, (1993), 68:3:327–332.

Chang YN et al., The palindromic series I repeats in the simian cytomegalovirus major immediate–early promoter behave as both strong basal enhancers and cyclic AMP response elements. *J Virol* 64(1):264–77, Jan. 1990.

Chu RS et al., CpG oligodeoxynucleotides act as adjuvants that switch on T helper 1 (Th1) immunity. *J Exp Med* 186(10):1623–31, Nov. 17, 1997.

Cowdery JS et al., Bacterial DNA induces NK cells to produce IFN–gamma in vivo and increases the toxicity of lipopolysaccharides. *J Immunol* 156(12):4570–5, Jun. 15, 1996.

Crosby et al., The Early Responses Gene FGFI–C Encodes a Zinc Finger Transcriptional Activator and is a Member of the GCGGGGCG (GSG) Element–Binding Protein Family. *Mol. Cell. Biol.*, 2:3835–3841, 1991.

Crystal, Transfer of Genes to Humans: Early Lessons and Obstacles to Success. *Science*, vol. 270, pp. 404–410, 1995.

D'Andrea A et al., Interleukin 10 (IL–10) inhibits human lymphocyte interferon gamma–production by suppressing natural killer cell stimulatory factory/IL–12 synthesis in accessory cells. *J Exp Med* 178(3):1041–8, 1993.

Englisch et al., Chemically Modified Oligonucleotides as Probes and Inhibitors, *Angew. Chem. Int. Ed. Engl.*, 30:613–629, 1991.

Erb KJ et al., Infection of mice with Mycobacterium bovis–Bacillus Calmette–Guerin (BCG) suppresses allergen–induced airway eosinophilia. *J Exp Med* 187(4):561–9, Feb. 16, 1998.

Etlinger, Carrier sequence selection—one key to successful vaccines, *Immunology Today*, vol. 13, 2:52–55, 1992.

Fox RI, Mechanism of action of hydroxychloroquine as an antirheumatic drug. *Chemical Abstracts*, 120:15, Abstract No. 182630 (Apr. 29, 1994).

Gao, W–Y et al., Phosphorothioate oligonucleotides are inhibitors of human DNA polymerases and Rnase H: Implications for antisense technology. *Mol. Pharmacol.* (1992), 41, 223–229.

Gura, T., Antisense Has Growing Pains. *Science* (1995), 270:575–576.

Hadden J et al., Immunostimulants. *TIPS*, (1993), 141:169–174.

Hadden J et al., Immunopharmacology, *JAMA*, (1992) 268:20:2964–2969.

Halpern MD et al., Bacterial DNA induces murine interferon–gamma production by stimulation of interleukin–12 and tumor necrosis factor–alpha. *Cell Immunol* 167(1):72–8, 1996.

Hatzfeld J., Release of Early Human Hematopoietic Progenitors from Quiescence by Antisense Transforming Growth Factor β1 or Rb Oligonucleotides, *J. Exp. Med.*, (1991) 174:925–929.

Highfield PE, Sepsis: the More, the Murkier, *Biotechnology*, 12:828, Aug. 12, 1994.

Hoeffler JP et al., Identification of multiple nuclear factors that interact with cyclic adenosine 3',5'–monophosphate response element–binding protein and activating transcription factor–2 by protein–protein interactions. *Mol Endocrinol* 5(2):256–66, Feb. 1991.

Horspool JH et al., Nucleic acid vaccine–induced immune resposnes require CD28 costimulation and are regulated by CTLA4. *J. Immunol*, 160, 2706–2714, 1998.

Iguchi–Ariga SM and Shaffner, W, CpG methylation of the cAMP–responsive enhancer/promoter sequence TGACGTCA abolishes specific factor binding as well as transcriptional activation. *Genes Dev* 3(5):612–9, May 1989.

Iverson, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43–52.

Ishikawa R et al., IFN induction and associated changes in splenic leukocyte distribution. *J Immunol.* 150(9):3713–27, May 1, 1993.

Jakway JP et al., Growth regulation of the B lymphoma cell line WEHI–231 by anti–immunoglobulin, lipopolysaccharide, and other bacterial products. *J. Immunol* 137(7):2225–31, Oct. 1, 1986.

Jones TR et al., Synthetic oligonucleotides containing CpG motifs enhance immunogenicity of a peptide malaria vaccine in Aotus monkeys. *Vaccine* 17, 3065–3071 1999.

Jaroszewski JW and Cohen JS, Cellular uptake of antisense oligonucleotides. *Adv Drug Delivery Rev* 6(3):235–50, 1991.

Kimura Y et al., Binding of Oligoguanylate to Scavenger Receptors Is Required for Oligonucleotides to Augment NK Cell Activity and Induce IFN, *J. Biochem.*, vol. 116, 5:991–994, 1994.

Kline JN et al., CpG motif oligonucleotides are effective in prevention of eosinophilic inflammation in a murine model of asthma. *J Invest Med* 44(7):380A, 1996.

Kline JN et al., Immune redirection by CpG oligonucleotides. Conversion of a Th2 response to a Th1 response in a murine model of asthma. *J Invest Med* 45(3):282A, 1997.

Kline JN et al., CpG oligonucleotides can reverse as well as prevent Th2–mediated inflammation in a murine model of asthma. *J Invest Med* 45(7):298A, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879–83, 1996.

Krieg AM, An innate immune defense mechanism based on the recognition of CpG motifs in microbial DNA. *J Lab Clin Med* 128(2):128–33, 1996.

Krieg AM et al., Uptake of oligodeoxyribonucleotides by lymphoid cells is heterogeneous and inducible. *Antisense Res Dev* 1(2):161–71, Summer 1991.

Krieg AM et al., Oligodeoxynucleotide modifications determine the magnitude of B cell stimulation by CpG motifs. *Antisense Nucleic Acid Drug Dev* 6(2):133–9, Summer 1996.

Krieg AM et al., "Modication of antisense phosphodiester oligodeoxynucleotides by a 5' cholesteryl moiety increases cellular association and improves efficacy", *Proc. Natl. Acad. Sci.*, (1993), 90:1048–1052.

Krieg AM et al., "CpG DNA: A Pathogenic Factor in Systemic Lupus Erythematosus?", *Journal of Clinical Immunology*, (1995) 15:6:284–292.

Krieg AM et al., Phosphorothioate Oligodeoxynucleotides: Antisense or Anti–Protein?, *Antisense Research and Develompent*, (1995), 5:241.

Krieg AM et al., "Leukocyte Stimulation by Oligodeoxynucleotides", *Applied Antisense Oligonucleotide Technology*, (1998), 431–448.

Krieg AM et al., CpG motifs in bacterial DNA trigger direct B–cell activation. *Nature* 374:546–9, 1995.

Krieg AM et al, "The role of CpG dinuleotides in DNA vaccines", Trends in Microbiology, vol. 6, pp. 23–27, Jan. 1998.

Krieg AM et al, A Role for Endogenous Retroviral Sequences in the Regulation of Lymphocyte Activation, the Journal of Immunology, vol. 143, 2448–2451, 1996.

Kuramoto et al., Oligonucleotide Sequences Required for Natural Killer Cell Activation, *Jpn. J. Cancer Res.*, 83:1128–1131, Nov. 1992.

Leonard et al., Conformation of Guanine 8–Oxoadenine Base Pairs in the Crystal Structure of d(CGCGAATT(08A)GCG). *Biochemistry*, 31(36):8415–8420, 1992.

Macfarlane DE and Manzel L, Antagonism of immunostimulatory CpG–oligodeoxynucleotides by quinacrine, chloroquine, and structurally related compounds. *J Immunol* 160(3):1122–31, Feb. 1, 1998.

Mastrangelo et al. *Seminars in Oncology.* vol. 23, 1:4–21, 1996.

Matson S and Krieg AM, Nonspecific suppression of [3H] thymidine incorporation by "control" oligonucleotides. *Antisense Res Dev* 2(4):325–30, Winter 1992.

Manzel.L and Macfarlane, DE, Lack of Immune Stimulation by Immobilized CpG–Oligonucleotide. *Antisense & Nucleic Acid Drug Development*, 459–464, 1999.

McIntyre KW et al., A sense phosphorothioate oligonucleotide directed to the initiation codon of transcription factor NF–kappa B p65 causes sequence–specific immune stimulation. *Antisense Res Dev* 3(4):309–22, Winter 1993.

Messina et al., The Influence of DNA Structure on the in vitro Stimulation of Murine Lymphocytes by Natural and Synthetic Polynucleotide Antigens. *Cellular Immunology*, 147:148–157, 1993.

Messina et al., Stimulation of in vitro Murine Lymphocyte Proliferation by Bacterial DNA. *J. Immunol.*, vol. 147, 6:1759–1764, Sep. 15, 1991.

Mojcik, C., et al., "Administration of a Phosphorothioate Oligonucleotide Antisense Murine Endogenous Retroviral MCF env Causes Immune Effect in vivo in a Sequence–Specific Manner", *Clinical Immunology and Immunopathology*, (1993), 67:2:130–136.

Mottram et al., A novel CDC2–related protein kinase from leishmania mexicana LmmCRK1 is post–translationally regulated during the life cycle. *J. Biol. chem.* 268:28, 21044–21052 (Oct. 1993).

*New England BIOLABS 1988–1989 Catalog.*

Nyce JW and Metzger WJ, DNA antisense therapy for asthma in an animal model. *Nature* 385:721–725, Feb. 20, 1997.

Pisetsky, D., "Stimulation of in vitro proliferation of murine lymphocytes by synthetic oligodeoxynucleotides", *Molecular Biology Repairs*, (1993) 18:217–221.

Pisetsky et al., Stimulation of Murine Lymphocyte Proliferation by a Phosphorothioate Oligonucleotide with Antisense Activity for Herpes Simplex Virus. *Life Science*, vol. 54, pp. 101–107 (1994).

Pisetsky, The Immunological Properties of DNA, *The Journal of Immunology*, pp. 421–423 (1996).

Pisetsky, Immunological Consequences of Nucleic Acid Therapy, *Antisense Research and Development*, 5:219–225 (1995).

Raz E et al., Preferential induction of a Th1 immune response and inhibition of specific IgE antibody formation by plasmid DNA immunization. *Proc Natl Acad Sci USA* 93(10):5141–5, May 14, 1996.

Roman M et al., Immunostimulatory DNA sequences function as T helper–1–promoting adjuvants. *Nat Med* 3(8):849–54, Aug. 1997.

Schnell et al., Identification and characterization of a Saccharomyces cerevisiae gene (PAR1) conferring resistance to iron chelators. *Eur. J. Biochem.*, 200:487–493.

Schwartz DA et al., Endotoxin responsiveness and grain dust–induced inflammation in the lower respiratory tract. *Am J Physiol* 267(5 Pt 1):L609–17, 1994.

Schwartz DA et al., The role of endotoxin in grain dust–induced lung disease. *Am J Respir Crit Care Med* 152(2):603–8, 1995.

Schwartz DA et al., CpG motifs in bacterial DNA cause inflammation in the lower respiratory tract. *J Clin Invest* 100(1):68–73, Jul. 1, 1997.

Shirakawa T et al., The inverse association between tuberculin responses and atopic disorder. *Science* 275(5296):77–9, Jan. 3, 1997.

Sparwasser T et al., Macrophages sense pathogens via DNA motifs: induction of tumor necrosis factor–alpha–mediated shock. *Eur J Immunol* 27(7):1671–9, Jul. 1997.

Stein CA et al., Oligonucleotides as inhibitors of gene expression: a review. *Cancer Research*, 48:2659–2668, 1988.

Stull et al., Antigene, Ribozyme, and Aptamer Nucleic Acid Drugs: Progress and Prospects, *Pharmaceutical Res.*, vol. 12, 4:465–483, 1995.

Subramanian et al., Theoretical Considerations on the "Spine of Hydration" in the Minor Groove of d(CGCGAATTCGCG) d(GCGCTTAAGCGC): Monte Carlo Computer Simulation. *Proc. Nat'l. Acad. Sci. USA*, 85:1836–1840, 1988.

Tanaka T et al., An antisense Oligonucleotide complementary to a sequence in IG2b increases G2b germline transcripts stimulates B cell DNA synthesis and inhibits immunoglobulin secretion. *J. Exp. Med.*, 175:597–607, 1992.

Thorne PS., Experimental grain dust atmospheres generated by wet and dry aerosolization techniques. *Am J Ind Med* 25(1):109–12, 1994.

Tokunaga T et al., Synthetic Oligonucleotides with Particular Base Sequences form the cDNA Encoding Proteins of *Myobacterium bovis* BCG Induce Interferons and Activate Natural Killer Cells, *Microbiol Immunol.*, vol. 36, 1:55–66, 1992.

Tokunaga et al., A Synthetic Single–Stranded DNA, Ply (dG, dC), Induces Interferon α/β and –γ, Augments Natural Killer Activity and Suppresses Tumor Growth. *Jpn. J. Cancer Res.*, 79:682–686, Jun. 1988.

Uhlmann et al., Antisense Oligonucleotides: A New Therapeutic Principle. *Chemical Reviews*, 90:543–584, 1990.

Wagner RW, Gene inhibition using antisense oligodeoxynucleotides. *Nature*, 372:L333–335, 1994.

Wallace et al., Oligonucleotide probes for the screening of recombinant DNA libraries. *Methods in Enzymology*, 152:432–442 (1987).

Weiss R., Upping the Antisense Ante: Scientists bet on profits from reverse genetics. *Science*, 139:108–109, 1991.

Whalen R, DNA Vaccines for Emerging Infection Diseases: What If?, *Emerging Infectious Disease*, vol. 2, 3:168–175, 1996.

Wooldridge, JE et al., Immunostimulatory oligodeoxynucleotides containing CpG motifs enhance the efficacy of monoclonal antibody therapy of lymphoma. *Blood*, 89:2994–2998, 1997.

Wu GY et al., Receptor–mediated gene delivery and expression in vivo. *J. Biol. Chem.*, 263:14621–14624, 1988.

Wu–Pong S., Oligonucleotides: Opportunities for Drug Therapy and Research. *Pharmacology Technology*, 18:102–114, 1994.

Yamamoto S et al., DNA from bacteria, but not from vertebrates, induces interferons, activates natural killer cells and inhibits tumor growth. *Microbiol Immunol* 36(9):983–97, 1992.

Yamamoto S et al., In vitro augmentation of natural killer cell activity and production of interferon–alpha/beta and – gamma with deoxyribonucleic acid fraction from *Mycobacterium bovis* BCG. *Jpn J Cancer Res* 79:866–73, Jul. 1988.

Yamamoto S., Mode of Action of Oligonucleotide Fraction Extracted from Mycobacterium bovis BCG, *Kekkaku*, vol. 69, 9:29–32, 1994.

Yamamoto S et al., Unique Palindromic Sequences in Synthetic Oligonucleotides are Required to Induce INF and Augment INF–Mediated Natural Killer Activity. *J. Immunol.*, vol. 148, 12:4072–4076, Jun. 15, 1992.

Yamamoto T et al., Ability of Oligonucleotides with Certain Palindromes to Induce Interferon Production and Augment Natural Killer Cell Activity is Associated with Their Base Length. *Antisense Res. and Devel.*, 4:119–123, 1994.

Yamamoto et al., Lipofection of Synthetic Oligodeoxyribonucleotide Having a Palindromic Sequence AACGTT to Murine Splenocytes Enhances Interferon Production and Natural Killer Activity. *Microbiol. Immunol.*, vol. 38, 10:831–836, 1994.

Yamamoto T et al., Synthetic Oligonucleotides with Certain Palindromes Stimulate Inteferon Production of Human Peripheral Blood Lymphocytes in vitro. *Jpn. J. Cancer Res.*, 85:775–779, 1994.

Yi, Ae–Kyung et al., IFN–γ Promotes IL–6 and IgM Secretion in Response to CpG Motifs in Bacterial DNA and Oligonucleotides, *The Journal of Immunology*, pp. 558–564 (1996).

Yi, Ai–Kyung et al., Rapid Immune Activation by CpG Motifs in Bacterial DNA, *The Journal of Immunology*, pp. 5394–5402 (1996).

Zhao Q et al., Stage–specific oligonucleotide uptake in murine bone marrow B–cell precursors. *Blood* 84(11):3660–6, Dec. 1, 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53–66, Spring 1993.

Xiang, Z et al. 1995 Immunity vol. 2, pp. 129–135.*

Sato, Y et al 1996 Science vol. 273, pp. 352–354.*

* cited by examiner

DEVELOPMENT OF ANTIBODY AFTER IMMUNIZATION WITH Id/GM-CSF + CpG ODN

DEVELOPMENT OF ANTIBODY AFTER REPEAT IMMUNIZATIONS WITH Id/GMCSF + CpG

CpG ODN ENHANCES THE PROTECTIVE EFFECT OF IMMUNIZATION WITH Id/GM-CSF

DENDRITIC CELLS PULSED WITH CpG ODN PRODUCE IL-12

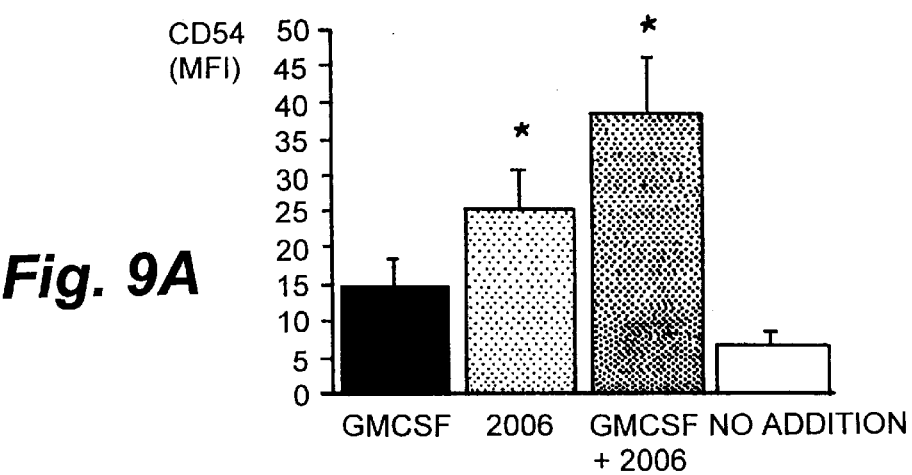
Fig. 9A
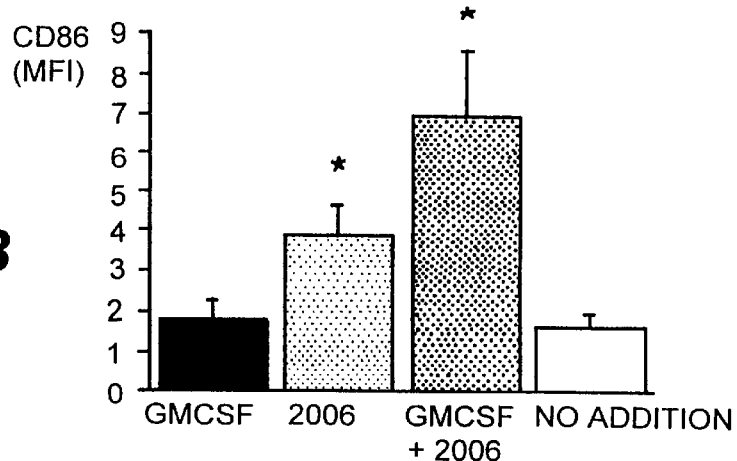
Fig. 9B
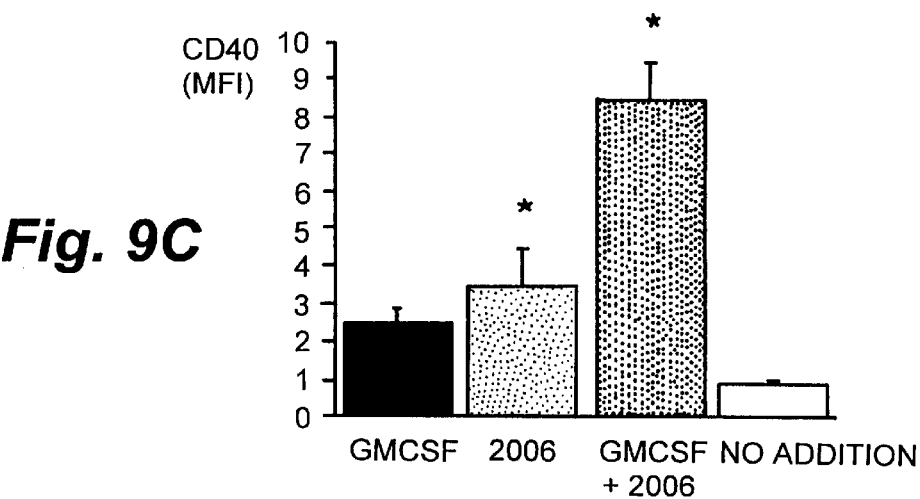
Fig. 9C
Fig. 9

SEQUENCE LISTING

<160> NUMBER OF SEQ ID NOS: 105

<210> SEQ ID NO: 1
<211> LENGTH: 15
<212> TYPE: DNA
<213> ORGANISM: Artificial Sequence
<220> FEATURE:
<223> OTHER INFORMATION: Synthetic Sequence

```
<400> SEQUENCE: 1
gctagacgtt agcgt                                                    15

<210> SEQ ID NO: 2
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 2
gctagatgtt agcgt                                                    15

<210> SEQ ID NO: 3
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<223> OTHER INFORMATION: Synthetic

<400> SEQUENCE: 3
gctagacgtt agcgt                                                    15

<210> SEQ ID NO: 4
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (13)...(13)
<223> OTHER INFORMATION: m5c

<400> SEQUENCE: 4
gctagacgtt agcgt                                                    15

<210> SEQ ID NO: 5
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 5
gcatgacgtt gagct                                                    15

<210> SEQ ID NO: 6
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 6
atggaaggtc cagcgttctc                                               20

<210> SEQ ID NO: 7
<211> LENGTH: 20
<212> TYPE: DNA
<213> ORGANISM: SArtificial Sequence
<220> FEATURE:
<223> OTHER INFORMATION: Synthetic Sequence
```

```
<400> SEQUENCE: 7
atcgactctc gagcgttctc                                               20

<210> SEQ ID NO: 8
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 8
atcgactctc gagcgttctc                                               20

<210> SEQ ID NO: 9
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: m5c

<400> SEQUENCE: 9
atcgactctc gagcgttctc                                               20

<210> SEQ ID NO: 10
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (18)...(18)
<223> OTHER INFORMATION: m5c

<400> SEQUENCE: 10
atcgactctc gagcgttctc                                               20

<210> SEQ ID NO: 11
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 11
atcgactctc gaacgttctc                                               20

<210> SEQ ID NO: 12
<211> LENGTH: 20
<212> TYPE: DNA
<213> ORGANISM: Artificial Sequence
<220> FEATURE:
```

```
<223> OTHER INFORMATION: Synthetic Sequence

<400> SEQUENCE: 12
gagaacgctg gaccttccat                                                    20

<210> SEQ ID NO: 13
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 13
gagaacgctc gaccttccat                                                    20

<210> SEQ ID NO: 14
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 14
gagaacgctc gaccttcgat                                                    20

<210> SEQ ID NO: 15
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 15
gagcaagctg gaccttccat                                                    20

<210> SEQ ID NO: 16
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (6)...(6)
OTHER INFORMATION: 5c

<400> SEQUENCE: 16
gagcacgctg gaccttccat                                                    20

<210> SEQ ID NO: 17
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (14)...(14)
OTHER INFORMATION: 5c

<400> SEQUENCE: 17
gagaacgctg gaccttccat                                                    20

<210> SEQ ID NO: 18
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 18
gagaacgatg gaccttccat                                               20

<210> SEQ ID NO: 19
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 19
gagaacgctc cagcactgat                                               20

<210> SEQ ID NO: 20
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 20
ccatgtcggt cctgatgct                                                19

<210> SEQ ID NO: 21
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 21
tccatgctgg tcctgatgct                                               20

<210> SEQ ID NO: 22
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (8)...(8)
<223> OTHER INFORMATION: m5c

<400> SEQUENCE: 22
tccatgtcgg tcctgatgct                                               20

<210> SEQ ID NO: 23
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (12)...(12)
<223> OTHER INFORMATION: m5c

<400> SEQUENCE: 23
tccatgtcgg tcctgatgct                                               20

<210> SEQ ID NO: 24
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 24
tccatgacgt tcctgatgct                                              20

<210> SEQ ID NO: 25
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 25
tccatgtcgg tcctgacgca                                              20

<210> SEQ ID NO: 26
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 26 tcaacgtt                                                            8

<210> SEQ ID NO: 27
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 27 tcaagctt                                                            8

<210> SEQ ID NO: 28
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 28 tcagcgct                                                            8

<210> SEQ ID NO: 29
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 29 tcttcgat                                                            8

<210> SEQ ID NO: 30
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 30 tcttcgaa                                                            8
```

```
<210> SEQ ID NO: 31
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 31 caacgtt                                                              7

<210> SEQ ID NO: 32
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 32 ccaacgtt                                                             8

<210> SEQ ID NO: 33
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 33 caacgttct                                                            9

<210> SEQ ID NO: 34
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 34 tcaacgtc                                                             8

<210> SEQ ID NO: 35
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 35
atggactctc cagcgttctc                                               20

<210> SEQ ID NO: 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
ataggaggtc caacgttctc                                               20

<210> SEQ ID NO: 37
<211> LENGTH: 20
<212> TYPE: DNA
<213> ORGANISM: Artificial Sequence
<220> FEATURE:
```

<223> OTHER INFORMATION: Synthetic Sequence

<400> SEQUENCE: 37
atcgactctc gagcgttctc                                          20

<210> SEQ ID NO: 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
atggaggctc catcgttctc                                          20

<210> SEQ ID NO: 39
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (11)...(11)
<223> OTHER INFORMATION: m5c
<220> FEATURE:
<221> NAME/KEY: modified_base
<222> LOCATION: (15)...(15)
<223> OTHER INFORMATION: m5c

<400> SEQUENCE: 39
atcggactct cgagcgttct c                                        21

<210> SEQ ID NO: 40
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (14)...(14)
<223> OTHER INFORMATION: m5c

<400> SEQUENCE: 40
atcgactctc gagcgttctc                                          20

<210> SEQ ID NO: 41
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 41
gcatgacgtt gagct                                               15

<210> SEQ ID NO: 42
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 42
tccatgtcgg tcctgatgct                                              20

<210> SEQ ID NO: 43
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 43
tccatgccgg tcctgatgct                                              20

<210> SEQ ID NO: 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
tccatggcgg tcctgatgct                                              20

<210> SEQ ID NO: 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
tccatgacgg tcctgatgct                                              20

<210> SEQ ID NO: 46
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 46
tccatgtcga tcctgatgct                                              20

<210> SEQ ID NO: 47
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 47
tccatgtcgc tcctgatgct                                              20

<210> SEQ ID NO: 48
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 48
tccatgtcgt tcctgatgct                                              20

<210> SEQ ID NO: 49
<211> LENGTH: 20
<212> TYPE: DNA

```
<213> ORGANISM: Artificial Sequence
<220> FEATURE:
<223> OTHER INFORMATION: Synthetic Sequence

<400> SEQUENCE: 49
tccataacgt tcctgatgct                                                    20

<210> SEQ ID NO: 50
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 50
tccatgacgt ccctgatgct                                                    20

<210> SEQ ID NO: 51
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 51
tccatcacgt gcctgatgct                                                    20

<210> SEQ ID NO: 52
<211> LENGTH: 19
<212> TYPE: DNA
<213> ORGANISM: Artificial Sequence
<220> FEATURE:
<223> OTHER INFORMATION: Synthetic  Sequence

<400> SEQUENCE: 52
ggggtcaacg ttgacgggg                                                     19

<210> SEQ ID NO: 53
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 53
ggggtcagtc gtgacgggg                                                     19

<210> SEQ ID NO: 54
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 54
gctagacgtt agtgt                                                         15

<210> SEQ ID NO: 55
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (7)...(7)
<223> OTHER INFORMATION: m5c
```

```
<400> SEQUENCE: 55
gctagacgtt agtgt                                                    15

<210> SEQ ID NO: 56
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 56
tccatgtcgt tcctgatgct                                               20

<210> SEQ ID NO: 57
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (8)...(8)
OTHER INFORMATION: 5c

<400> SEQUENCE: 57
tccatgtcgt tcctgatgct                                               20

<210> SEQ ID NO: 58
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 58
accatggacg atctgtttcc cctc                                          24

<210> SEQ ID NO: 59
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 59
tctcccagcg tgcgccat                                                 18

<210> SEQ ID NO: 60
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 60
taccgcgtgc gaccctct                                                 18

<210> SEQ ID NO: 61
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 61
```

-continued accatggacg aactgttttcc cctc                                      24

<210> SEQ ID NO: 62
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 62
accatggacg agctgtttcc cctc                                       24

<210> SEQ ID NO: 63
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 63
accatggacg acctgtttcc cctc                                       24

<210> SEQ ID NO: 64
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 64
accatggacg tactgtttcc cctc                                       24

<210> SEQ ID NO: 65
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 65
accatggacg gtctgtttcc cctc                                       24

<210> SEQ ID NO: 66
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 66
accatggacg ttctgtttcc cctc                                       24

<210> SEQ ID NO: 67
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 67
cacgttgagg ggcat                                                 15

<210> SEQ ID NO: 68
<211> LENGTH: 15
<212> TYPE: DNA
<213> ORGANISM: Artificial Sequence

```
<220> FEATURE:
<223> OTHER INFORMATION: Synthetic Sequence

<400> SEQUENCE: 68
ctgctgagac tggag                                                    15

<210> SEQ ID NO: 69
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 69
tcagcgtgcg cc                                                       12

<210> SEQ ID NO: 70
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 70
atgacgttcc tgacgtt                                                  17

<210> SEQ ID NO: 71
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 71
tctcccagcg ggcgcat                                                  17

<210> SEQ ID NO: 72
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 72
tctcccagcg cgcgccat                                                 18

<210> SEQ ID NO: 73
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 73
tccatgtcgt tcctgtcgtt                                               20

<210> SEQ ID NO: 74
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 74
tccatagcgt tcctagcgtt                                               20
```

<210> SEQ ID NO: 75
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 75
tcgtcgctgt ctccgcttct t                                   21

<210> SEQ ID NO: 76
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 76
tcctgacgtt cctgacgtt                                      19

<210> SEQ ID NO: 77
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 77
tcctgtcgtt cctgtcgtt                                      19

<210> SEQ ID NO: 78
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 78
tccatgtcgt ttttgtcgtt                                     20

<210> SEQ ID NO: 79
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 79
tcctgtcgtt ccttgtcgtt                                     20

<210> SEQ ID NO: 80
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 80
tccttgtcgt tcctgtcgtt                                     20

<210> SEQ ID NO: 81
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 81
tcctgtcgtt ttttgtcgtt                                    20

<210> SEQ ID NO: 82
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 82
tcgtcgctgt ctgcccttct t                                  21

<210> SEQ ID NO: 83
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 83
tcgtcgctgt tgtcgtttct t                                  21

<210> SEQ ID NO: 84
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (8)...(8)
OTHER INFORMATION: 5c
<220> FEATURE:
<221> NAME/KEY: modified_base
U<222> LOCATION: (17)...(17)
<223> OTHER INFORMATION: m5c

<400> SEQUENCE: 84
tccatgtcgt tcctgtcgtt                                    20

<210> SEQ ID NO: 85
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 85
tccaggactt ctctcaggtt                                    20

<210> SEQ ID NO: 86
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 86
tccatgcgtg cgtgcgtttt                                    20

<210> SEQ ID NO: 87
<211> LENGTH: 20
<212> TYPE: DNA
<213> ORGANISM: Artificial Sequence
<220> FEATURE:

-continued

<223> OTHER INFORMATION: Synthetic Sequence

<400> SEQUENCE: 87
tccatgcgtt gcgttgcgtt                                    20

<210> SEQ ID NO: 88
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 88
tccacgacgt tttcgacgtt                                    20

<210> SEQ ID NO: 89
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 89
tcgtcgttgt cgttgtcgtt                                    20

<210> SEQ ID NO: 90
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 90
tcgtcgtttt gtcgttttgt cgtt                               24

<210> SEQ ID NO: 91
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 91
tcgtcgttgt cgttttgtcg tt                                 22

<210> SEQ ID NO: 92
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 92
gcgtgcgttg tcgttgtcgt t                                  21

<210> SEQ ID NO: 93
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 93
gcggcgggcg gcgcgcgccc                                    20

<210> SEQ ID NO: 94
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 94
tgtcgtttgt cgtttgtcgt t                                    21

<210> SEQ ID NO: 95
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 95
tgtcgttgtc gttgtcgttg tcgtt                                25

<210> SEQ ID NO: 96
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 96
tgtcgttgtc gttgtcgtt                                       19

<210> SEQ ID NO: 97
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 97
tcgtcgtcgt cgtt                                            14

<210> SEQ ID NO: 98
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 98
tgtcgttgtc gtt                                             13

<210> SEQ ID NO: 99
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 99
tccatagcgt tcctagcgtt                                      20

```
<210> SEQ ID NO :100
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 100
tccatgacgt tcctgacgtt                                           20

<210> SEQ ID NO :101
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 101 gtcgyt                                                           6

<210> SEQ ID NO :102
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 102 tgtcgyt                                                          7

<210> SEQ ID NO :103
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 103
tccatgagct tcctgagtct                                           20

<210> SEQ ID NO :104
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 104
tctcccagcg tgcgccat                                             18

<210> SEQ ID NO: 105
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 105
tccatgacgt tcctgacgtt                                           20
```

METHODS AND PRODUCTS FOR STIMULATING THE IMMUNE SYSTEM USING IMMUNOTHERAPEUTIC OLIGONUCLEOTIDES AND CYTOKINES

RELATED APPLICATIONS

This application claims priority under 35 U.S.C. 119(e) to U.S. provisional patent application Ser. No. 60/080,729, filed Apr. 3, 1998.

FIELD OF THE INVENTION

The present invention relates to synergistic combinations of immunostimulatory CpG oligonucleotides and immunopotentiating cytokines. In particular, the invention relates to methods of stimulating an immune response using the synergistic combination of compounds and products related thereto.

BACKGROUND OF THE INVENTION

The theory of immune surveillance is that a prime function of the immune system is to detect and eliminate neoplastic cells before a tumor forms. A basic principle of this theory is that cancer cells are antigenically different from normal cells and thus elicit immune reactions that are similar to those that cause rejection of immunologically incompatible allografts. Studies have confirmed that tumor cells differ, either qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., caricnoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen dependent nor MHC restricted once activated. Activated macrophages are through to decrease the growth rate of the tumors they infiltrate. In vitro assays have identified other immune mechanisms such as antibody-dependent, cell-mediated cytotoxic reactions and lysis by antibody plus complement. However, these immune effector mechanisms are thought to be less important in vivo than the function of NK, CTLs, LAK, and macrophages in vivo (for review see Piessens, W. F., and David, J., "Tumor Immunology", In: *Scientific American Medicine*, Vol. 2, Scientific American Books, N.Y., pp. 1–13, 1996.

One of the most complex phenomenon in cancer immunology relates to the failure of the immune system to eliminate tumors. In the 1970's, Hewitt articulated the notion that most tumors did not express any tumor-specific or neoantigens and, thus, could not be recognized as "foreign" by the immune system. Indeed, virtually no tumor cell surface antigens recognized by antibodies were found to be tumor specific, and furthermore, most spontaneous murine tumors were considered "poorly immunogenic" as defined by their failure to be eliminated when transferred into syngeneic hosts (Hewitt, et al., *Br. J. Cancer,* 33:241–259, 1976). However, these same tumors could be rendered "immunogenic" by mutagenesis (Van Pel and Boon, *Proc. Natl. Acad. Sci. USA,* 79:4718–4722, 1982) when new antigens were expressed on the tumor cells surface. It is possible that the immune system fails to eliminate tumors not because neoantigens are absent, but rather because in vivo the response to antigens is inadequate. Therefore, a method for enhancing immunogenicity of the tumor cells by potentiating the host's immune response to the tumor cells would provide a key advance in immunotherapy.

The goal of immunotherapy is to augment a patient's immune response to an established tumor. One method of immunotherapy includes the use of adjuvants. Adjuvant substances derived from microorganisms, such as bacillus Calmette-Guerin, heighten the immune response and enhance resistance to tumors in animals. Although bacillus Calmette-Guerin has been tested in many clinical trials, the results have been inconclusive, and the value of this type of bacterial adjuvant therapy remains uncertain (Piessens and David, 1996, supra).

A number of bacterial products, such as lipopolysaccharide, are known to stimulate mammalian immune responses. Recently, bacterial DNA itself has been reported to be one such molecule (e.g., Krieg, A. M., et al., 1995, *Nature* 374:546–9). One of the major differences between bacterial DNA, which has potent immunostimulator effects, and vertebrate DNA, which does not, is that bacterial DNA contains a higher frequency of unmethylated CpG dinucleotides than does vertebrate DNA. Select synthetic oligodeoxynucleotides (ODN) containing unmethylated CpG motifs (CpG ODN) have been shown to have an immunologic effects and can induce activation of B cells, NK cells and antigen-presenting cells (APCs) such as monocytes and macrophages (Krieg, A. M., et al., supra). It can also enhance production of cytokines known to participate in the development of an active immune response, including tumor necrosis factor-α, IL-12 and IL-6 (e.g., Klinman D. M., et al., *Proc. Natl. Acad. Sci. USA,* 93:2879–83, 1996).

The binding of DNA to cells has been shown to be similar to a ligand receptor interaction: binding is saturable, competitive, and leads to DNA endocytosis and degradation into oligonucleotides (Benne, R. M., et al., *J. Clin. Invest.* 76:2182, 1995). Like DNA, oligodeoxyribonucleotides are able to enter cells in a process which is sequence, temperature, and energy independent (Jaroszewski and Cohen, *Ad. Drug. Del. Rev.* 6:235, 1991). Lymphocyte oligodeoxyribonucleotide uptake has been shown to be regulated by cell activation (Krieg, A. M., et al., *Antisense Research and Development* 1:161, 1991).

GM-CSF is known to regulate cell proliferation under basal and stress conditions, and is known to activate the tumoricidal activity of macrophages. Some studies indicate that simultaneous treatment with GM-CSF and standard induction chemotherapy may improve the efficacy of chemotherapy (Estey, E. H., *Blood* 83:2015, 1994). The major benefit of colony stimulating factors, such as GM-CSF, has been postulated to be their use in the treatment pancytopenia, one of the complications of chemotherapy (Piessens and David, 1996, supra).

SUMMARY OF THE INVENTION

The present invention relates to methods and products for inducing a synergistic immune response using a combination of a CpG oligonucleotide and a cytokine. In one aspect the invention is a method for stimulating an immune response in a subject. The method includes the steps of administering to a subject exposed to an antigen an effective amount for inducing a synergistic antigen specific immune response of an immunopotentiating cytokine and an immunostimulatory CpG oligonucleotide having a sequence including at least the following formula:

$$5' \; X_1 CG X_2 \; 3'$$

wherein the oligonucleotide includes at least 8 nucleotides wherein C and G are unmethylated and wherein $X_1$ and $X_2$ are nucleotides.

The cytokine may, for instance be GM-CSF, IL-3, IL-5, IL-12, or interferon-γ. The immunopotentiating cytokine may also be an antigen-cytokine fusion protein. In a preferred embodiment the antigen-cytokine fusion protein is an antigen-GM-CSF fusion protein.

The antigen may be any type of antigen known in the art. In one embodiment the antigen is a selected from the group consisting of a tumor antigen, a microbial antigen, and an allergen. Preferably the antigen is a tumor antigen. In this embodiment the subject may have a neoplastic disorder. In other embodiments the antigen is a viral antigen and the subject has or is at risk of having a viral infection.

In some embodiments the antigen is administered to the subject in conjunction with the immunostimulatory CpG oligonucleotide and the immunopotentiating cytokine. In other embodiments the subject is passively exposed to the antigen.

In other aspects the invention is a composition of an effective amount for synergistically activating a dendritic cell of an immunostimulatory CpG oligonucleotide having a sequence including at least the following formula:

$$5' \; X_1 CG X_2 \; 3'$$

wherein the oligonucleotide includes at least 8 nucleotides wherein C and G are unmethylated and wherein $X_1$ and $X_2$ are nucleotides; and a cytokine selected from the group consisting of GM-CSF, IL-4, TNFα, Flt3 ligand, and IL-3. Preferably the cytokine is GM-CSF.

The composition may also include an antigen. In some embodiments the antigen is selected from the group consisting of a cancer antigen, a microbial antigen, and an allergen.

A method for activating a dendritic cell is provided according to another aspect of the invention. The method includes the step of contacting a dendritic cell exposed to an antigen with an effective amount for synergistically activating a dendritic cell of an immunopotentiating cytokine and an immunostimulatory CpG oligonucleotide having a sequence including at least the following formula:

$$5' \; X_1 CG X_2 \; 3'$$

wherein the oligonucleotide includes at least 8 nucleotides wherein C and G are unmethylated and wherein $X_1$ and $X_2$ are nucleotides.

The cytokine may, for instance be GM-CSF, IL-3, IL-5, IL-12, or interferon-γ. The immunopotentiating cytokine may also be an antigen-cytokine fusion protein. In a preferred embodiment the antigen-cytokine fusion protein is an antigen-GM-CSF fusion protein.

The antigen may be any type of antigen known in the art. In one embodiment the antigen is a selected from the group consisting of a tumor antigen, a microbial antigen, and an allergen. Preferably the antigen is a tumor antigen. In this embodiment the subject may have a neoplastic disorder. In other embodiments the antigen is a viral antigen and the subject has or is at risk of having a viral infection.

According to another aspect the invention is a method for treating a subject having a neoplastic disorder. The method includes the step of administering to the tumor of a subject having a neoplastic disorder an immunopotentiating cytokine and an immunostimulatory CpG oligonucleotide having a sequence including at least the following formula:

$$5' \; X_1 CG X_2 \; 3'$$

wherein the oligonucleotide includes at least 8 nucleotides wherein C and G are unmethylated and wherein $X_1$ and $X_2$ are nucleotides, in an amount effective for synergistically increasing survival time of the subject with respect to a subject administered the immunostimulatory CpG oligonucleotide or the immunopotentiating cytokine alone.

Preferably the tumor is selected from the group consisting of a tumor of the brain, lung, ovary, breast, prostate, colon, skin, and blood. In one embodiment the immunostimulatory CpG oligonucleotide and the immunopotentiating cytokine are injected directly into the tumor.

A contraceptive method is provided in another aspect of the invention. The method involves the step of administering to a subject an antigen, an immunopotentiating cytokine and an immunostimulatory CpG oligonucleotide having a sequence including at least the following formula:

$$5' \; X_1 CG X_2 \; 3'$$

wherein the oligonucleotide includes at least 8 nucleotides wherein C and G are unmethylated and wherein $X_1$ and $X_2$ are nucleotides, wherein the antigen is an antigen selected from the group consisting of a gonadal cell antigen and an antigen from a cytokine or hormone required for the maintenance of a gonadal cell.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 9 is several graphs depicting induction of co-stimulatory molecule expression on dendritic cells by CpG. Dendritic precursor cells were incubated for 48 hours in the presence of GM-CSF (800 U/ml) and oligonucleotides (2006: CpG phosphorothioate, 6 μg/ml) as indicated. Expression of CD54 (ICAM-1) (panel A), CD86 (B7-2) (panel B) and CD40 (panel C) was quantified by flow cytometry (MFI, mean fluorescence intensity). The combination of GM-CSF and 2006 shows synergy for increasing the expression of CD86 and CD40, while the effect on CD54 was additive. Results represent the mean of 5 independent experiments (CD54 and CD86) and 4 experiments (CD40). Statistical significance of the increase compared to the cell only sample is indicated by * (p<0.05). Statistical evaluation is performed by the unpaired t-test, error bars indicate SEM.

DETAILED DESCRIPTION OF THE INVENTION

The invention relates to methods and products for stimulating an immune response in a subject. It was discovered according to the invention that synergistic responses to combinations of immunopotentiating compounds could be achieved. These synergistic effects were observed in vitro, in vivo and ex vivo. A synergistic increase in survival rate was even observed in animals having an established tumor. The method is performed by administering to the subject who has been exposed to an antigen an effective amount for inducing a synergistic antigen specific immune response of an immunopotentiating cytokine and an immunostimulatory CpG oligonucleotide.

Figure 3:
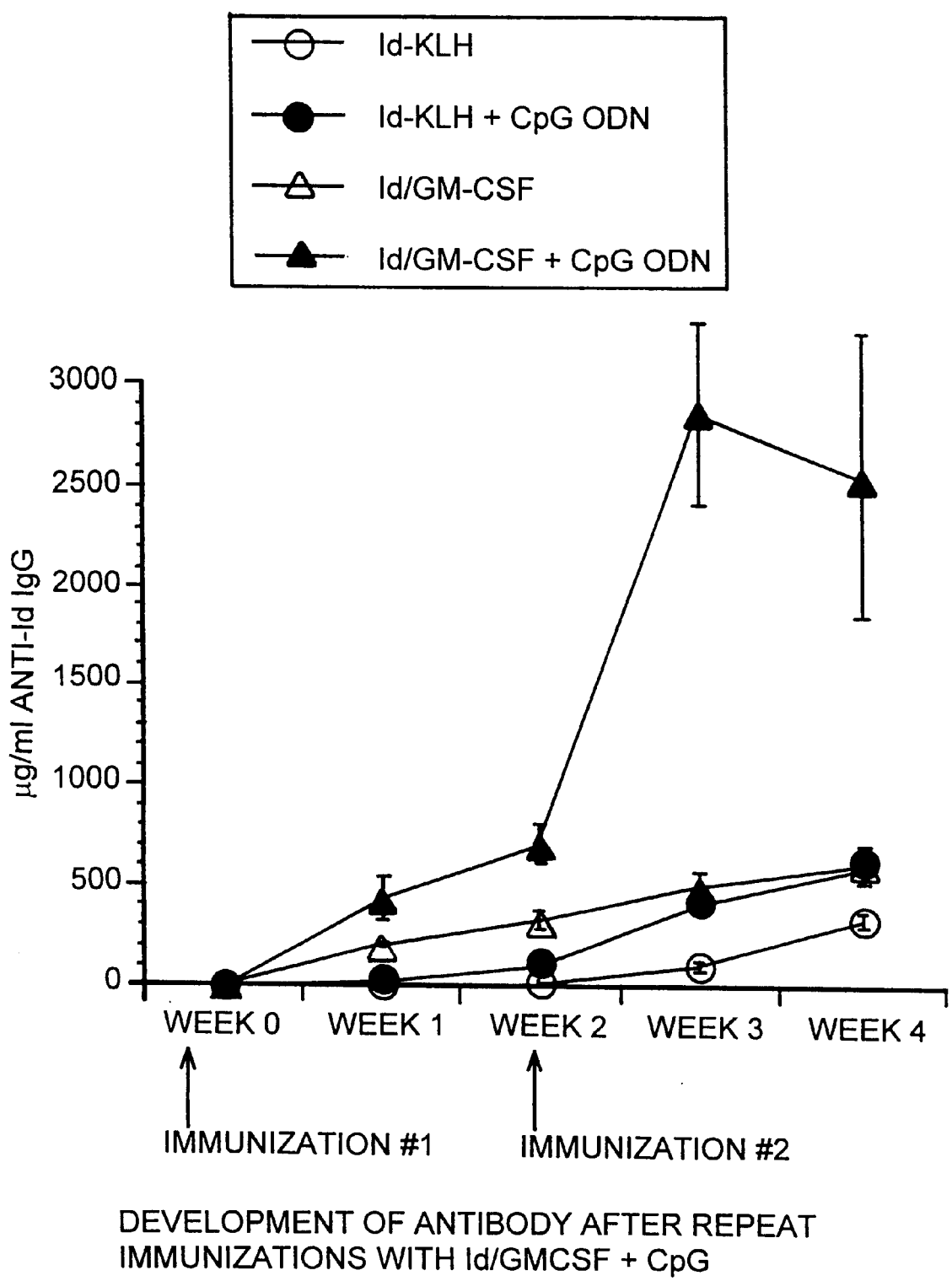
FIG. 3 is a graph showing that immunization using repeated immunizations with a combination of Id/GM-CSF fusion protein and CpG ODN induces high levels of antigen-specific IgG. Mice were immunized with 50 μg of Id/GM-CSF as a subcutaneous dose with or without CpG ODN on week 0 and again on week 2. Blood was obtained weekly, and serum was evaluated for the presence of anti-Id IgG by ELISA. Normal mouse serum supplemented with a known concentration of monoclonal anti-Id was used as a standard. Three mice were included in each group.

The finding is based on the discovery that when an immunostimulatory CpG oligonucleotide is administered to a subject in combination with an immunopotentiating cytokine the resultant immune response is synergistic. Both CpG oligonucleotides and immunopotentiating cytokines have the ability to produce immune responses on their own when administered to a subject. When the combination of the two is administered together, however, the quantity and type of immune response shifts. For instance, when the CpG oligonucleotide and immunopotentiating cytokine are administered in conjunction with an antigen using repeat immunizations, as shown in FIG. 3, a synergistic induction in antigen specific IgG is observed. Additionally, when CpG and GM-CSF are administered together an antibody response develops that includes both IgG2a (indicative of a Th1 immune response) and IgG1 (indicative of a Th2 immune response) whereas when GM-CSF is administered alone IgG2a antibodies are undetectable or low depending on the strain of the animal.

Amazingly, the combination of a CpG oligonucleotide and immunopotentiating cytokine has a dramatic effect on the survival rate of animals injected with a tumor, even when administered several days after tumor inoculation. The finding was remarkable because it demonstrated that the combination of drugs was able to eliminate an established tumor. Typical prior art immunization strategies generally are performed prior to inoculation to prevent the establishment of a tumor. When mice were injected with a tumor and not provided with any subsequent tumor therapy the survival rate was 0%. Mice treated with CpG oligonucleotide alone or GM-CSF and antigen had survival rates of 0 and 30% respectively. The combination of CpG oligonucleotide and GM-CSF produced a dramatic survival rate of 70%. This finding has serious implications for the treatment of established tumors as well as for the prevention of tumor development.

The invention in one aspect is a method for stimulating an immune response in a subject. The method is performed by administering to the subject who has been exposed to an antigen an effective amount for inducing a synergistic antigen specific immune response of an immunopotentiating cytokine and an immunostimulatory CpG oligonucleotide. The immunostimulatory CpG oligonucleotide has a sequence including at least the following formula:

wherein the oligonucleotide includes at least 8 nucleotides wherein C and G are unmethylated and wherein $X_1$ and $X_2$ are nucleotides.

An "antigen" as used herein is a molecule capable of provoking an immune response. Antigens include but are not limited to cells, cell extracts, polysaccharides, polysaccharide conjugates, lipids, glycolipids, carbohydrate, peptides, proteins, viruses, and viral extracts. The term antigen broadly includes any type of molecule which is recognized by a host immune system as being foreign. Antigens include but are not limited to cancer antigens, microbial antigens, and allergens.

The methods of the invention are useful for treating cancer by stimulating an antigen specific immune response against a cancer antigen. A "cancer antigen" as used herein is a compound, such as a peptide, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research*, 54:1055, by partially purifying the antigens, by recombinant technology, or by de novo synthesis of known antigens. Cancer antigens include antigens that are immunogenic portions of or are a whole tumor or cancer. Such antigens can be isolated or prepared recombinately or by any other means known in the art. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Tumors are antigenic and can be sensitive to immunological destruction. The term "tumor" is usually equated with neoplasm, which literally means "new growth" and is used interchangeably with "cancer." A "neoplastic disorder" is any disorder associated with cell proliferation, specifically with a neoplasm. A "neoplasm" is an abnormal mass of tissue that persists and proliferates after withdrawal of the carcinogenic factor that initiated its appearance. There are two types of neoplasms, benign and malignant. Nearly all benign tumors are encapsulated and are noninvasive; in contrast, malignant tumors are almost never encapsulated but invade adjacent tissue by infiltrative destructive growth. This infiltrative growth can be followed by tumor cells implanting at sites discontinuous with the original tumor. The method of the invention can be used to treat neoplastic disorders in humans, including but not limited to: sarcoma, carcinoma, fibroma, lymphoma, melanoma, neuroblastoma, retinoblastoma, and glioma as well as each of the other tumors described herein.

The invention can also be used to treat cancer and tumors in non human subjects. Cancer is one of the leading causes of death in companion animals (i.e., cats and dogs). Cancer usually strikes older animals which, in the case of house pets, have become integrated into the family. Forty-five % of dogs older than 10 years of age, are likely to succomb to the disease. The most common treatment options include surgery, chemotherapy and radiation therapy. Others treatment modalities which have been used with some success are laser therapy, cryotherapy, hyperthermia and immunotherapy. The choice of treatment depends on type of cancer and degree of dissemination. Unless the malignant growth is confined to a discrete area in the body, it is difficult to remove only malignant tissue without also affecting normal cells.

Malignant disorders commonly diagnosed in dogs and cats include but are not limited to lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilms tumor, Burkitt's lymphoma, microglioma, neuroblastoma, osteoclastoma, oral neoplasia, fibrosarcoma, osteosarcoma and rhabdomyosarcoma. Other neoplasias in dogs include genital squamous cell carcinoma, transmissable veneral tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an evermore popular house pet is known to develop insulinoma, lymphoma, sarcoma, neuroma, pancreatic islet cell tumor, gastric MALT lymphoma and gastric adenocarcinoma.

Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lumphadenitis (CLA): chronic, infectious, contagious disease of sheep and goats caused by the bacterium *Corynebacterium pseudotuberculosis*, and contagious lung tumor of sheep caused by jaagsiekte.

CpG oligonucleotide can be useful in activating B cells, NK cells, and antigen-presenting cells, such as monocytes and macrophages. CpG oligonucleotide enhances antibody dependent cellular cytotoxicity and can be used as an adjuvant in conjunction with tumor antigen to protect against a tumor challenge (Wooldridge, J. E., et al., 1987, supra; Weiner, G. J., et al., *Proc. Natl. Acad. Sci. USA* 94:10833–10837, 1997). This invention is based on the finding that CpG oligonucleotide and an immunopotentiating cytokine act synergistically in order to produce an immune response against a tumor, such that the effect of CpG oligonucleotide and the immunopotentiating agent is greater than the sum of the individual effects of either CPG oligonucleotide or the immunopotentiating agent.

In the method of the invention, CpG oligonucleotide are used with an immunopotentiating cytokine. "Immunopotentiating cytokines" are those molecules and compounds which stimulate the humoral and/or cellular immune response. The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, granulocyte-macrophage colony stimulating factor (G-MCSF), granulocyte colony stimulating factor (GCSF), interferon-γ (γ-INF), tumor necrosis factor (TNF), TGF-β, FLT-3 ligand, and CD40 ligand.

FLT3 ligand is a class of compounds described in EP0627487A2 and WO94/28391. A human FLT3 ligand cDNA was deposited with the American Tissue Type Culture Collection, Rockville, Md., and assigned accession number ATCC 69382. Interleukins (Ils) have been described extensively in the art, e.g., Mosley, et al., 1989, *Cell*, 59:335, Idzerda, et al., 1990, *J. Exp. Med.,* 171:861. GM-CSF is commercially available as sargramostine, leukine (Immunex).

Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. Th1 cells express IL-3, IL4, IL-5, IL-6, IL-9, IL-10, IL-13, GM-CSF and low levels of TNF-α. The TH1 subset promotes delayed-type hypersensitivity, cell-mediated immunity, and immunoglobulin class switching to $IgG_{2a}$. The Th2 subset induces humoral immunity by activating B cells, promoting antibody production, and inducing class switching to $IgG_1$ and IgE.

Tumors can express "Tumor-specific antigens" which are antigens that can potentially stimulate apparently tumor-specific immune responses. These antigens can be encoded by normal genes and fall into several categories (1) normally silent genes, (2) differentiation antigens (3) embryonic and fetal antigens, and (4) clonal antigens, which are expressed only on a few normal cells such as the cells from which the tumor originated. Tumor-specific antigens can be encoded by mutant cellular genes, such as oncogenes (e.g., activated ras oncogene), suppressor genes (e.g., mutant p53), fusion proteins resulting from internal deletions or chromosomal translocations. Tumor-specific antigens can also be encoded by viral genes, such as RNA or DNA tumor viruses.

In the treatment of lymphoma, the idiotype of the secreted immunoglobulin serves as a highly specific tumor associated antigen. By "idiotype" is meant the collection of V-region determinants specific to a specific antibody or a limited set of antibodies. In one embodiment, the immunopotentiating cytokine is a protein (a fusion protein) consisting of a specific antigen idiotype secreted by a lymphoma fused to the immunopotentiating cytokine. Methods of producing antigen-cytokine fusion proteins are well known in the art (e.g., Tao, M. H., Levy, R., *Nature* 362:755–758, 1993). In one embodiment, the fusion protein is an antigen-GM-CSF fusion protein.

The methods of the invention are also useful for treating infectious diseases. An infectious disease, as used herein, is a disease arising from the presence of a foreign microorganism in the body. CpG and immunopotentiating cytokine are used to stimulate an antigen specific immune response which can activate a T or B cell response against an antigen of the microorganism. The methods are accomplished in the same way as described above for the tumor except that the antigen is specific for a microorganism using a microbial antigen. A "microbial antigen" as used herein is an antigen of a microorganism and includes but is not limited to infectious virus, infectious bacteria, and infectious fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of infectious virus that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to Pasteurella species, Staphylococci species, and Streptococcus species. Gram negative bacteria include, but are not limited to, *Escherichia coli*, Pseudomonas species, and Salmonella species. Specific examples of infectious bacteria include but are not limited to: *Helicobacter pyloris, Borelia burgdorferi, Legionella pneumophilia*, Mycobacteria sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter Sp., Enterococcus sp., *Haemophilus influenzae, Bacillus antracis, Corynebacterium diphtheriae*, Corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, Rickettsia, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: Plasmodium such as *Plasmodium falciparum, Plasmodium malariae, Plasmodium ovale*, and *Plasmodium vivax* and *Toxoplasma gondii.*

Other medically relevant microorganisms have been descried extensively in the literature, e.g., see C. G. A. Thomas, *Medical Microbiology*, Bailliere Tindall, Great Britain 1983, the entire contents of which is hereby incorporated by reference.

The methods of the invention are also useful for treating allergic diseases. The methods are accomplished in the same way as described above for the tumor immunotherapy and treatment of infectious diseases except that the antigen is specific for an allergen. Currently, allergic diseases are generally treated by the injection of small doses of antigen followed by subsequent increasing dosage of antigen. It is believed that this procedure produces a memory immune response to prevent further allergic reactions. These methods, however, are associated with the risk of side effects such as an allergic response. The methods of the invention avoid these problems.

An "allergen" refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); Dermatophagoides (e.g. *Dermatophagoides farinae*); Felis (*Felis domesticus*); Ambrosia (*Ambrosia artemiisfolia*); Lolium (e.g. *Lolium perenne* or *Lolium multiflorum*); Cryptomeria (*Cryptomeria japonica*); Alternaria (*Alternaria alternata*); Alder; Alnus (*Alnus gultinoasa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

An "allergy" refers to acquired hypersensitivity to a substance (allergen). Allergic conditions include but are not limited to eczema, allergic rhinitis or coryza, hay fever, bronchial asthma, urticaria (hives) and food allergies, and other atopic conditions. A subject having an allergic reaction is a subject that has or is at risk of developing an allergy.

Allergies are generally caused by IgE antibody generation against harmless allergens. The cytokines that are induced by unmethylated CpG oligonucleotides are predominantly of a class called "Th1" which is most marked by a cellular immune response and is associated with IL-12 and IFN-γ and production of IgG2a antibody. The other major type of immune response is termed as Th2 immune response, which is associated with more of an IgG1 antibody immune response and with the production of IL4, IL-5 and IL-10. In general, it appears that allergic diseases are mediated by Th2 type immune responses and autoimmune diseases by Th1 immune response. Based on the ability of the combination of CpG oligonucleotides and immunopotentiating cytokine to shift the immune response in a subject from a Th2 (which is associated with production of IgE antibodies and allergy and is produced in response to GM-CSF alone) to a Th1 response (which is protective against allergic reactions), an effective dose of a CpG oligonucleotide and immunopotentiating cytokine can be administered to a subject to treat or prevent an allergy.

CpG oligonucleotides combined with immunopotentiating cytokines may also have significant therapeutic utility in the treatment of asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. "Asthma" refers to a disorder of the respiratory system characterized by inflammation, narrowing of the airways and increased reactivity of the airways to inhaled agents. Asthma is frequently, although not exclusively associated with atopic or allergic symptoms.

As described in co-pending patent application U.S. Ser. No. 08/960,774, oligonucleotides containing an unmethylated CpG motif (i.e. TCCATGACGTTCCTGACGTT; SEQ ID NO: 93), but not a control oligonucleotide (TCCATGAGCTTCCTGAGTCT; SEQ ID NO: 103) prevented the development of an inflammatory cellular infiltrate and eosinophilia in a murine model of asthma. Furthermore, the suppression of eosinophilic inflammation was associated with a suppression of Th2 response and induction of a Th1 response.

A "subject" shall mean a human or vertebrate animal including but not limited to a dog, cat, horse, cow, pig, sheep, goat, chicken, primate, e.g., monkey, fish (aquaculture species), e.g. salmon, rat, and mouse.

Although many of the disorders described above relate to human disorders, the invention is also useful for treating other nonhuman vertebrates. Nonhuman vertebrates are also capable of developing cancer, infections, allergies, and asthma. For instance, in addition to the treatment of infectious human diseases, the methods of the invention are useful for treating infections of animals.

As used herein, the term "treat", "treated", or "treating" when used with respect to an infectious disease refers to a prophylactic treatment which increases the resistance of a subject to infection with a pathogen or, in other words, decreases the likelihood that the subject will become infected with the pathogen as well as a treatment after the subject has become infected in order to fight the infection, e.g., reduce or eliminate the infection or prevent it from becoming worse. Many vaccines for the treatment of non-human vertebrates are disclosed in Bennett, K. *Compendium of Veterinary Products,* 3rd ed. North American Compendiums, Inc., 1995.

Thus the present invention contemplates the use of CpG oligonucleotides and immunopotentiating cytokines to induce an antigen specific immune response in human and non-human animals. As discussed above, antigens include infectious microbes such as virus, bacteria and fungi and fragments thereof, derived from natural sources or synthetically. Infectious virus of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting.

In addition to the use of the combination of CpG oligonucleotides and immunopotentiating cytokines to induce an antigen specific immune response in humans, the methods of the preferred embodiments are particularly well suited for treatment of birds such as hens, chickens, turkeys, ducks, geese, quail, and pheasant. Birds are prime targets for many types of infections.

Hatching birds are exposed to pathogenic microorganisms shortly after birth. Although these birds are initially protected against pathogens by maternal derived antibodies, this protection is only temporary, and the bird's own immature immune system must begin to protect the bird against the pathogens. It is often desirable to prevent infection in young birds when they are most susceptible. It is also desirable to prevent against infection in older birds, especially when the birds are housed in closed quarters, leading to the rapid spread of disease. Thus, it is desirable to administer the CpG oligonucleotide and the immunopotentiating cytokine of the invention to birds to enhance an antigen-specific immune response when antigen is present.

An example of a common infection in chickens is chicken infectious anemia virus (CIAV). CIAV was first isolated in Japan in 1979 during an investigation of a Marek's disease vaccination break (Yuasa et al., 1979, Avian Dis. 23:366–385). Since that time, CIAV has been detected in commercial poultry in all major poultry producing countries (van Bulow et al., 1991, pp. 690–699) in Diseases of Poultry, 9th edition, Iowa State University Press).

CIAV infection results in a clinical disease, characterized by anemia, hemorrhage and immunosuppression, in young susceptible chickens. Atrophy of the thymus and of the bone marrow and consistent lesions of CIAV-infected chickens are also characteristic of CIAV infection. Lymphocyte depletion in the thymus, and occasionally in the bursa of Fabricius, results in immunosuppression and increased susceptibility to secondary viral, bacterial, or fungal infections which then complicate the course of the disease. The immunosuppression may cause aggravated disease after infection with one or more of Marek's disease virus (MDV), infectious bursal disease virus, reticuloendotheliosis virus, adenovirus, or reovirus. It has been reported that pathogenesis of MDV is enhanced by CIAV (DeBoer et al., 1989, p. 28 In Proceedings of the 38th Western Poultry Diseases Conference, Tempe, Ariz.). Further, it has been reported that CIAV aggravates the signs of infectious bursal disease (Rosenberger et al., 1989, Avian Dis. 33:707–713). Chickens develop an age resistance to experimentally induced disease due to CAA. This is essentially complete by the age of 2 weeks, but older birds are still susceptible to infection (Yuasa, N. et al., 1979 supra; Yuasa, N. et al., Arian Diseases 24, 202–209, 1980). However, if chickens are dually infected with CAA and an immunosuppressive agent (IBDV, MDV etc.) age resistance against the disease is delayed (Yuasa, N. et al., 1979 and 1980 supra; Bulow von V. et al., J. Veterinary Medicine 33, 93–116, 1986). Characteristics of CIAV that may potentiate disease transmission include high resistance to environmental inactivation and some common disinfectants. The economic impact of CIAV infection on the poultry industry is clear from the fact that 10% to 30% of infected birds in disease outbreaks die.

Vaccination of birds, like other vertebrate animals can be performed at any age. Normally, vaccinations are performed at up to 12 weeks of age for a live microorganism and between 14–18 weeks for an inactivated microorganism or other type of vaccine. For in ovo vaccination, vaccination can be performed in the last quarter of embryo development. The vaccine may be administered subcutaneously, by spray, orally, intraocularly, intratracheally, nasally, in ovo or by other methods described herein. Thus, the CpG oligonucleotide and immunopotentiating cytokine of the invention can be administered to birds and other non-human vertebrates using routine vaccination schedules and the antigen is administered after an appropriate time period as described herein.

Cattle and livestock are also susceptible to infection. Disease which affect these animals can produce severe economic losses, especially amongst cattle. The methods of the invention can be used to protect against infection in livestock, such as cows, horses, pigs, sheep, and goats.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the pestivirus genus. Although, Pestiviruses were previously classified in the Togaviridae family, some studies have suggested their reclassification within the Flaviviridae family along with the flavivirus and hepatitis C virus (HCV) groups (Francki, et al., 1991).

BVDV, which is an important pathogen of cattle can be distinguished, based on cell culture analysis, into cytopathogenic (CP) and noncytopathogenic (NCP) biotypes. The NCP biotype is more widespread although both biotypes can be found in cattle. If a pregnant cow becomes infected with an NCP strain, the cow can give birth to a persistently infected and specifically immunotolerant calf that will spread virus during its lifetime. The persistently infected cattle can succumb to mucosal disease and both biotypes can then be isolated from the animal. Clinical manifestations can include abortion, teratogenesis, and respiratory problems, mucosal disease and mild diarrhea. In addition, severe thrombocytopenia, associated with herd epidemics, that may result in the death of the animal has been described and strains associated with this disease seem more virulent than the classical BVDVs.

Equine herpesviruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Primary infection of upper respiratory tract of young horses results in a febrile illness which lasts for 8 to 10 days. Immunologically experienced mares may be reinfected via the respiratory tract without disease becoming apparent, so that abortion usually occurs without warning. The neurological syndrome is associated with respiratory disease or abortion and can affect animals of either sex at any age, leading to incoordination, weakness and posterior paralysis (Telford, E. A. R. et al., Virology 189, 304–316, 1992). Other EHV's include EHV-2, or equine cytomegalovirus, EHV-3, equine coital exanthema virus, and EHV-4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al. (1990) Lancet 36:1538–1541; Desrosiers et al. PNAS USA (1989) 86:6353–6357; Murphey-Corb et al. (1989) Science 246:1293–1297; and Carlson et al. (1990) AIDS Res. Human Retroviruses 6:1239–1246). A recombinant HIV gp120 vaccine has been reported to afford protection in chimpanzees (Berman et al. (1990) Nature 345:622–625).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to prevent them against infection.

Domestic cats may become infected with several retroviruses, including but not limited to feline leukemia virus (FeLV), feline sarcoma virus (FeSV), endogenous type C oncornavirus (RD-114), and feline syncytia-forming virus (FeSFV). Of these, FeLV is the most significant pathogen, causing diverse symptoms, including lymphoreticular and myeloid neoplasms, anemias, immune mediated disorders, and an immunodeficiency syndrome which is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (also referred to as feline immunodeficiency) was first reported in Pedersen et al. (1987) Science 235:790–793. Characteristics of FIV have been reported in Yamamoto et al. (1988) Leukemia, December Supplement 2:204S–215S; Yamamoto et al. (1988) Am. J. Vet. Res. 49:1246–1258; and Ackley et al. (1990) J. Virol. 64:5652–5655. Cloning and sequence analysis of FIV have been reported in Olmsted et al. (1989) Proc. Natl. Acad. Sci. USA 86:2448–2452 and 86:4355–4360.

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old.

Viral and bacterial diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Nucleic acid based vaccinations are described in U.S. Pat. No. 5,780,448 issued to Davis.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered orally or by immersion or injection.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

Polypeptides of viral aquaculture pathogens include but are not limited to glycoprotein (G) or nucleoprotein (N) of viral hemorrhagic septicemia virus (VHSV); G or N proteins of infectious hematopoietic necrosis virus (IHNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Polypeptides of bacterial pathogens include but are not limited to an iron-regulated outer membrane protein, (IROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (IROMP), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of Rickettsia.

Polypeptides of a parasitic pathogen include but are not limited to the surface antigens of Ichthyophthirius.

The subject is exposed to the antigen. As used herein, the term "exposed to" refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG and immunopotentiating cytokine are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface. When a subject is passively exposed to an antigen it is preferred that the CpG oligonucleotide is an oligonucleotide of 8–100 nucleotides in length and/or has a phosphate modified backbone.

The methods in which a subject is passively exposed to an antigen can be particularly dependent on timing of CpG oligonucleotide and immunopotentiating cytokine administration. For instance, in a subject at risk of developing a cancer or an infectious disease or an allergic or asthmatic response, the subject may be administered the CpG oligonucleotide and immunopotentiating cytokine on a regular basis when that risk is greatest, i.e., during allergy season or after exposure to a cancer causing agent. Additionally the CpG oligonucleotide and immunopotentiating cytokine may be administered to travelers before they travel to foreign lands where they are at risk of exposure to infectious agents. Likewise the CpG oligonucleotide and immunopotentiating cytokine may be administered to soldiers or civilians at risk of exposure to biowarfare to induce a systemic immune response to the antigen when and if the subject is exposed to it.

A subject at risk of developing a cancer can also be treated according to the methods of the invention, by passive or active exposure to antigen following CpG and immunopotentiating cytokine. A subject at risk of developing a cancer is one who is who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins. When a subject at risk of developing a cancer is treated with CpG and immunopotentiating cytokine on a regular basis, such as monthly, the subject will be able to recognize and produce an antigen specific immune response. If a tumor begins to form in the subject, the subject will develop a specific immune response against one or more of the tumor antigens. This aspect of the invention is particularly advantageous when the antigen to which the subject will be exposed is unknown. For instance, in soldiers at risk of exposure to biowarfare, it is generally not known what biological weapon to which the soldier might be exposed.

The antigen may be delivered to the immune system of a subject alone or with a carrier. For instance, colloidal dispersion systems may be used to deliver antigen to the subject. As used herein, a "colloidal dispersion system" refers to a natural or synthetic molecule, other than those derived from bacteriological or viral sources, capable of delivering to and releasing the antigen in a subject. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2–4.0µ can encapsulate large macromolecules within the aqueous interior and these macromolecules can be delivered to cells in a biologically active form (Fraley, et al., *Trends Biochem. Sci.*, 6:77 (1981)).

Lipid formulations for transfection are commercially available from QIAGEN, for example as EFFECTENE™ (a non-liposomal lipid with a special DNA condensing enhancer) and SUPER-FECT™ (a novel acting dendrimeric technology) as well as Gibco BRL, for example, as LIPO-FECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes were described in a review article by Gregoriadis, G., *Trends in Biotechnology* 3:235–241 (1985), which is hereby incorporated by reference.

It is envisioned that the antigen may be delivered to the subject in a nucleic acid molecule which encodes for the antigen such that the antigen must be expressed in vivo. In these embodiments of the invention the nucleic acids molecule may also include a CpG dinucleotide within the sequence of the nucleic acid. But in this case the nucleic acid molecule does not take the place of the CpG oligonucleotide. The antigen must be administered in conjunction with a CpG oligonucleotide that is separate from the nucleic acid molecule. The nucleic acid encoding the antigen is operatively linked to a gene expression sequence which directs the expression of the antigen nucleic acid within a eukaryotic cell. The "gene expression sequence" is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

The antigen nucleic acid is operatively linked to the gene expression sequence. As used herein, the antigen nucleic acid sequence and the gene expression sequence are said to be "operably linked" when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the antigen sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a gene expression sequence would be operably linked to an antigen nucleic acid sequence if the gene expression sequence were capable of effecting transcription of that antigen nucleic acid sequence such that the resulting transcript is translated into the desired protein or polypeptide.

The antigen nucleic acid of the invention may be delivered to the immune system alone or in association with a vector. In its broadest sense, a "vector" is any vehicle capable of facilitating the transfer of the antigen nucleic acid to the cells of the immune system and preferably APCs so that the antigen can be expressed and presented on the surface of an APC. Preferably, the vector transports the nucleic acid to the immune cells with reduced degradation relative to the extent of degradation that would result in the absence of the vector. The vector optionally includes the above-described gene expression sequence to enhance expression of the antigen nucleic acid in APCs. In general, the vectors useful in the invention include, but are not limited to, plasmids, phagemids, viruses, other vehicles derived from viral or bacterial sources that have been manipulated by the insertion or incorporation of the antigen nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman C.O., New York (1990) and Murry, E. J. Ed. "Methods in Molecular Biology," vol. 7, Humana Press, Inc., Clifften, N.J. (1991).

A preferred virus for certain applications is the adeno-associated virus, a double-stranded DNA virus. The adeno-associated virus can be engineered to be replication-deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and ligation reactions to remove and add specific fragments of DNA.

It has recently been discovered that gene carrying plasmids can be delivered to the immune system using bacteria. Modified forms of bacteria such as Salmonella can be transfected with the plasmid and used as delivery vehicles. The bacterial delivery vehicles can be administered to a host subject orally or by other administration means. The bacteria deliver the plasmid to immune cells, e.g. dendritic cells, probably by passing through the gut barrier. High levels of immune protection have been established using this methodology.

Thus, the invention contemplates scheduled administration of CpG oligonucleotides and immunopotentiating cytokine. The oligonucleotides may be administered to a subject on a weekly or monthly basis. When a subject is at risk of exposure to an antigen or antigens the CpG and immunopotentiating cytokine may be administered on a regular basis to recognize the antigen immediately upon exposure and produce an antigen specific immune response. A subject at risk of exposure to an antigen is any subject who has a high probability of being exposed to an antigen and of developing an immune response to the antigen. If the antigen is an allergen and the subject develops allergic responses to that particular antigen and the subject is exposed to the antigen, i.e., during pollen season, then that subject is at risk of exposure to the antigen.

The CpG oligonucleotides of the invention are nucleic acid molecules which contain an unmethylated cytosine-guanine dinucleotide sequence (i.e. "CpG DNA" or DNA containing a 5' cytosine followed by 3' guanosine and linked by a phosphate bond) and activate the immune system. The CpG oligonucleotides can be double-stranded or single-stranded. Generally, double-stranded molecules are more stable in vivo, while single-stranded molecules have increased immune activity.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g. genomic or cDNA), but are preferably synthetic (e.g. produced by oligonucleotide synthesis). The entire CpG "oligonucleotide can be unmethylated or portions may be unmethylated but at least the C of the 5' CG 3' must be unmethylated.

In one preferred embodiment the invention provides a CpG oligonucleotide represented by at least the formula:

wherein at least one nucleotide separates consecutive CpGs; $X_1$ is adenine, guanine, or thymine; $X_2$ is cytosine, adenine, or thymine; N is any nucleotide and $N_1$ and $N_2$ are nucleic acid sequences composed of from about 0–25 N's each.

In another embodiment the invention provides an isolated CpG oligonucleotide represented by at least the formula:

wherein at least one nucleotide separates consecutive CpGs; $X_1X_2$ is selected from the group consisting of GpT, GpA, ApA, GpG and ApT; $X_3X_4$ is selected from the group consisting of TpT, CpT, TpC, CpC, and ApT; N is any nucleotide and $N_1$ and $N_2$ are nucleic acid sequences composed of from about 0–25 N's each. In a preferred embodiment $N_1$ and $N_2$ of the nucleic acid do not contain a CCGG quadmer or more than one CCG or CGG trimer. In another preferred embodiment the CpG oligonucleotide has the sequence 5'$TCN_1TX_1X_2CGX_3X_4$3'.

Preferably the CpG oligonucleotides of the invention include $X_1X_2$ selected from the group consisting of GpT, GpG, GpA and ApA and $X_3X_4$ is selected from the group consisting of TpT, CpT and GpT. For facilitating uptake into cells, CpG containing oligonucleotides are preferably in the range of 8 to 30 bases in length. However, nucleic acids of any size greater than 8 nucleotides (even many kb long) are capable of inducing an immune response according to the invention if sufficient immunostimulatory motifs are present, since larger nucleic acids are degraded into oligonucleotides inside of cells. Preferred synthetic oligonucleotides do not include a CCGG quadmer or more than one CCG or CGG trimer at or near the 5' and/or 3' terminals. Stabilized oligonucleotides, where the oligonucleotide incorporates a phosphate backbone modification, as discussed in more detail below are also preferred. The modification may be, for example, a phosphorothioate or phosphorodithioate modification. Preferably, the phosphate backbone modification occurs at the 5' end of the nucleic acid for example, at the first two nucleotides of the 5' end of the oligonucleotide. Further, the phosphate backbone modification may occur at the 3' end of the nucleic acid for example, at the last five nucleotides of the 3' end of the nucleic acid. Alternatively the oligonucleotide may be completely or partially modified.

Preferably the CpG oligonucleotide is in the range of between 8 and 100 and more preferably between 8 and 30 nucleotides in size. Alternatively, CpG oligonucleotides can be produced on a large scale in plasmids and degraded into oligonucleotides.

The CpG oligonucleotide and immunopotentiating cytokine may be directly administered to the subject or may be administered in conjunction with a nucleic acid delivery complex. A "nucleic acid/cytokine delivery complex" shall mean a nucleic acid molecule and/or cytokine associated with (e.g. ionically or covalently bound to; or encapsulated within) a targeting means (e.g. a molecule that results in higher affinity binding to target cell (e.g. dendritic cell surfaces and/or increased cellular uptake by target cells). Examples of nucleic acid/cytokine delivery complexes include nucleic acids/cytokines associated with: a sterol (e.g. cholesterol), a lipid (e.g. a cationic lipid, virosome or liposome), or a target cell specific binding agent (e.g. a ligand recognized by target cell specific receptor). Preferred complexes should be sufficiently stable in vivo to prevent significant uncoupling prior to internalization by the target cell. However, the complex should be cleavable under appropriate conditions within the cell so that the nucleic acid/cytokine is released in a functional form.

"Palindromic sequence" shall mean an inverted repeat (i.e. a sequence such as ABCDEE'D'C'B'A' in which A and A' are bases capable of forming the usual Watson-Crick base pairs. In vivo, such sequences may form double-stranded structures. In one embodiment the CpG oligonucleotide contains a palindromic sequence. A palindromic sequence used in this context refers to a palindrome in which the CpG is part of the palindrome, and preferably is the center of the palindrome. In another embodiment the CpG oligonucleotide is free of a palindrome. A CpG oligonucleotide that is free of a palindrome is one in which the CpG dinucleotide is not part of a palindrome. Such an oligonucleotide may include a palindrome in which the CpG is not part of the palindrome.

A "stabilized nucleic acid molecule" shall mean a nucleic acid molecule that is relatively resistant to in vivo degradation (e.g. via an exo- or endo-nuclease). Stabilization can be a function of length or secondary structure. Unmethylated CpG oligonucleotides that are tens to hundreds of kbs long are relatively resistant to in vivo degradation. For shorter CpG oligonucleotides, secondary structure can stabilize and increase their effect. For example, if the 3' end of an oligonucleotide has self-complementarity to an upstream region, so that it can fold back and form a sort of stem loop structure, then the oligonucleotide becomes stabilized and therefore exhibits more activity.

Preferred stabilized oligonucleotides of the instant invention have a modified backbone. It has been demonstrated that modification of the oligonucleotide backbone provides enhanced activity of the CpG oligonucleotides when administered in vivo. CpG constructs, including at least two phosphorothioate linkages at the 5' end of the oligonucleotide in multiple phosphorothioate linkages at the 3' end, preferably 5, provides maximal activity and protected the oligonucleotide from degradation by intracellular exo- and endo-nucleases. Other modified oligonucleotides include phosphodiester modified oligonucleotide, combinations of phosphodiester and phosphorothioate oligonucleotide, methylphosphonate, methylphosphorothioate, phosphorodithioate, and combinations thereof. Each of these combinations and their particular effects on immune cells is discussed in more detail in copending PCT Published Patent Applications claiming priority to U.S. Ser. Nos. 08/738,652 and 08/960,774, filed on Oct. 30, 1996 and Oct. 30, 1997 respectively, the entire contents of which is hereby incorporated by reference. It is believed that these modified oligonucleotides may show more stimulatory activity due to enhanced nuclease resistance, increased cellular uptake, increased protein binding, and/or altered intracellular localization.

Both phosphorothioate and phosphodiester oligonucleotides containing CpG motifs are active in APCs such as dendritic cells. However, based on the concentration needed to induce CpG specific effects, the nuclease resistant phosphorothioate backbone CpG oligonucleotides are more potent (2 μg/ml for the phosphorothioate vs. a total of 90 μg/ml for phosphodiester).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

The nucleic acid sequences of the invention which are useful for inducing immune remodeling are those broadly described above and disclosed in PCT Published Patent Applications claiming priority to U.S. Ser. Nos. 08/738,652 and 08/960,774, filed on Oct. 30, 1996 and Oct. 30, 1997 respectively. Exemplary sequences include but are not limited to those immunostimulatory sequences shown in Table 1 as well as TCCATGTCGCTCCTGATGCT (SEQ ID NO: 47), TCCATGTCGTTCCTGATGCT (SEQ ID NO: 48), TCGTCGTTTTGTCGTTTTGTCGTT (SEQ ID NO: 53), TCGTCGTTGTCGTTGTCGTT (SEQ ID NO: 89); TCGTCGTTTTGTCGTTTTGTCGTT (SEQ ID NO: 90), TCGTCGTTGTCGTTTTGTCGTT (SEQ ID NO: 91), GCGTGCGTTGTCGTTGTCGTT (SEQ ID NO: 92), TGTCGTTTGTCGTTTGTCGTT (SEQ ID NO: 94), TGTCGTTGTCGTTGTCGTT (SEQ ID NO: 96), TCGTCGTCGTCGTT (SEQ ID NO:97), TCCTGTCGT-TCCTTGTCGTT (SEQ ID NO: 79), TCCT-GTCGTTTTTTGTCGTT (SEQ ID NO:81), TCGTCGCT-GTCTGCCCTTCTT (SEQ ID NO:82), TCGTCGCTGTTGTCGTTTCTT (SEQ ID NO:83), TCGTCGTTTTGTCGTTTTGTCGTT (SEQ ID NO:90), TCGTCGTTGTCGTTTTGTCGTT (SEQ ID NO:91), TGTCGTTGTCGTTGTCGTT (SEQ ID NO:96), TCCAT-GACGTTCCTGACGTT (SEQ ID NO:100), GTCG(T/C)T (SEQ ID NO:101) and TGTCG(T/C)T (SEQ ID NO: 102).

The stimulation index of a particular immunostimulatory CpG DNA can be tested in various immune cell assays. Preferably, the stimulation index of the immunostimulatory CpG DNA with regard to B cell proliferation is at least about 5, preferably at least about 10, more preferably at least about 15 and most preferably at least about 20 as determined by incorporation of $^3$H uridine in a murine B cell culture, which has been contacted with 20 $\mu$M of oligonucleotide for 20 h at 37° C. and has been pulsed with 1 $\mu$Ci of $^3$H uridine; and harvested and counted 4 h later as described in detail in copending PCT Patent Application U.S. Ser. No. 08/960, 774. For use in vivo, for example, to treat an immune system deficiency by stimulating a cell-mediated (local) immune response in a subject, it is important that the immunostimulatory CpG DNA be capable of effectively inducing cytokine secretion by APCs such as dendritic cells.

Preferred immunostimulatory CpG nucleic acids should effect at least about 500 pg/ml of TNF-$\alpha$, 15 pg/ml IFN-$\gamma$, 70 pg/ml of GM-CSF 275 pg/ml of IL-6, 200 pg/ml IL-12, depending on the therapeutic indication, as determined by the assays described in the Examples. Other preferred immunostimulatory CpG DNAs should effect at least about 10%, more preferably at least about 15% and most preferably at least about 20% YAC-1 cell specific lysis or at least about 30, more preferably at least about 35 and most preferably at least about 40% 2C11 cell specific lysis. When administered in conjunction with an immunopotentiating cytokine the amounts of both the CpG oligonucleotide and the cytokine required to produce a desired immune response will be less.

Preferably, the stimulation index of the CpG oligonucleotide with regard to B cell proliferation is at least about 5, preferably at least about 10, more preferably at least about 15 and most preferably at least about 20 as determined by incorporation of $^3$H uridine in a murine B cell culture, which has been contacted with 20 $\mu$M of oligonucleotide for 20 h at 37° C. and has been pulsed with 1 $\mu$Ci of $^3$H uridine; and harvested and counted 4 h later as described in detail in copending PCT Published Patent Applications claiming priority to U.S. Ser. Nos. 08/738,652 and 08/960,774, filed on Oct. 30, 1996 and Oct. 30, 1997 respectively. For use in vivo, for example, it is important that the CpG oligonucleotide and cytokine be capable of effectively inducing activation of APC's such as dendritic cells. Oligonucleotides which can accomplish this are, for example, those oligonucleotides described in PCT Published Patent Applications claiming priority to U.S. Ser. Nos. 08/738,652 and 08/960, 774, filed on Oct. 30, 1996 and Oct. 30, 1997 respectively.

CpG oligonucleotides and immunopotentiating cytokines can be administered to a subject alone prior to the administration of an antigen. The oligonucleotides and cytokines can also be administered to a subject in conjunction with an antigen to provide an immediate antigen specific response. A second antigen which may be the same or different from the first antigen may then be administered to the subject at some time point after the administration of CpG and immunopotentiating cytokine in the presence or absence of additional CpG and cytokine. The term "in conjunction with" refers to the administration of the CpG oligonucleotide and immunopotentiating cytokine slightly before or slightly after or at the same time as the antigen. The terms slightly before and slightly after refer to a time period of 24 hours and preferably 12 hours. The CpG and cytokine are administered in conjunction with one another and thus may also be administered together or separately.

When the CpG oligonucleotide and immunopotentiating cytokine are administered in conjunction with a first antigen the first antigen will determine the specificity of the immediate immune response. The CpG oligonucleotide and immunopotentiating cytokine act as an effective "danger signal" and cause the immune system to respond vigorously to new antigens in the area. This mode of action presumably results primarily from the stimulatory local effects of CpG oligonucleotide and immunopotentiating cytokine on dendritic cells and other "professional" antigen presenting cells, as well as from the co-stimulatory effects on B cells. This effect occurs immediately upon the administration of the CpG oligonucleotide.

For use in therapy, an effective amount of an appropriate CpG oligonucleotide and immunopotentiating cytokine alone or formulated as a nucleic acid/cytokine delivery complex can be administered to a subject by any mode allowing the oligonucleotide to be taken up by the appropriate target cells (e.g. dendritic cells). Preferred routes of administration include but are not limited to oral, transdermal (e.g. via a patch), injection (subcutaneous, intravenous, parenteral, intraperitoneal, intrathecal, etc.), intranasal, intratracheal, and mucosal. An injection may be in a bolus or a continuous infusion.

The term "effective amount" of a CpG oligonucleotide refers to the amount necessary or sufficient to realize a desired biologic effect. For example, an effective amount of an oligonucleotide containing at least one unmethylated CpG for treating an immune system deficiency could be that amount necessary to cause activation of the immune system, resulting in the development of an antigen specific immune response upon exposure to antigen. An effective amount as used herein is an amount that produces a synergistic immune response. A synergistic amount is that amount which produces an immune response against a specific antigen that is greater than the sum of the individual effects of either the CpG or the cytokine alone.

The effective amount for any particular application can vary depending on such factors as the disease or condition being treated, the particular CpG oligonucleotide/cytokine being administered (e.g. the number of unmethylated CpG motifs or their location in the nucleic acid), the size of the subject, or the severity of the disease or condition. One of ordinary skill in the art can empirically determine the effective amount of a particular oligonucleotide/cytokine without necessitating undue experimentation.

Another use for CpG oligonucleotide in combination with an immunopotentiating cytokine is the production of a contraceptive method for use in a subject. In this particular embodiment, the subject is preferably mammalian, and preferably nonhuman. The testes and ovaries are "immune privileged," that is they are separated anatomically from the immune system. In addition, cells in the testes and the ovaries can express fas ligand, which induces apoptosis in activated T cells. The physical separation and the expression of fas ligand both prevent an immune response against the cells in the testes and ovaries. The CpG oligonucleotide used in conjunction with an immunopotentiating cytokine can be used to eliminate or substantially reduce the cells in the testes and the ovaries by breaking the immune privilege of these cells, thereby providing a contraceptive means. CpG oligonucleotide can be used in conjunction with an immunopotentiating cytokine to break the immune privilege of the cells of the testes and ovaries.

The method is accomplished by administering to a subject an antigen, an immunopotentiating cytokine and an immunostimulatory CpG oligonucleotide, wherein the antigen is an antigen selected from the group consisting of a gonadal cell antigen and an antigen from a cytokine or hormone required for the maintenance of a gonadal cell. A "gonadal cell antigen" as used herein is an antigen on the surface of a gonadal cell, e.g., testis or ovary cell. Such antigens are well known to those of skill in the art. Antigens from a cytokine or hormone required for the maintenance of a gonadal cell are also well known in the art. These antigens will cause an immune response against the cytokine or hormone thus causing a loss of gonadal cells.

The CpG oligonucleotides are used in one aspect of the invention to induce activation of immune cells and preferably APCs. An APC has its ordinary meaning in the art and includes, for instance, dendritic cells such as immature dendritic cells and precursor and progenitor dendritic cells, as well as mature dendritic cells which are capable of taking up and expressing antigen. Such a population of APC or dendritic cells is referred to as a primed population of APCs or dendritic cells.

Dendritic cells form the link between the innate and the acquired immune system by presenting antigens as well as through their expression of pattern recognition receptors which detect microbial molecules like LPS in their local environment. The combination of immunopotentiating cytokine and CpG oligonucleotide showed induction of Th1 specific antibody when immunopotentiating cytokine alone only produced Th2 specific antibody. Since dendritic cells form the link between the innate and the acquired immune system the ability to activate dendritic cells with CpG and immunopotentiating cytokine supports the use of combination CpG-immunopotentiating cytokine based strategies for immunotherapy against disorders such as cancer and allergic or infectious diseases. The combination of CpG and immunopotentiating cytokine shows synergistic activation of dendritic cells.

The invention relates in one aspect to methods and products for activating dendritic cells for in vitro, ex vivo and in vivo purposes. It was demonstrated according to the invention that the combination of immunopotentiating cytokine and CpG oligonucleotide is a potent activator of dendritic cells. Dendritic cells are believed to be essential for the initiation of primary immune responses in immune cells in vivo. It was discovered, according to the invention, that CpG oligonucleotides and immunopotentiating cytokine were capable of activating dendritic cells to initiate primary immune responses in T cells, similar to an adjuvant. It was also discovered that when the combination of the CpG oligonucleotide and immunopotentiating cytokine is used to activate dendritic cells the production of predominantly IgG2a and less IgG1 is induced, indicating its propensity to augment the development of Th1 immune responses in vivo. These findings demonstrate the potent adjuvant activity of CpG and provide the basis for the use of CpG oligonucleotides as immunotherapeutics in the treatment of disorders such as cancer, infectious diseases, and allergy. In one aspect, the invention is a method for activating a dendritic cell by contacting the dendritic cell which is exposed to an antigen with an effective amount for synergistically activating a dendritic cell of an immunopotentiating cytokine and an immunostimulatory CpG oligonucleotide.

Dendritic cells efficiently internalize, process, and present soluble specific antigen to which it is exposed. The process of internalizing and presenting antigen causes rapid upregulation of the expression of major histocompatibility complex (MHC) and costimulatory molecules, the production of cytokines, and migration toward lymphatic organs where they are believed to be involved in the activation of T cells.

One specific use for the combination of CpG oligonucleotide and immunopotentiating cytokine of the invention is to activate dendritic cells for the purpose of enhancing a specific immune response against cancer antigens. The immune response may be enhanced using ex vivo or in vivo techniques. An "ex vivo" method as used herein is a method which involves isolation of a dendritic cell from a subject, manipulation of the cell outside of the body, and reimplantation of the manipulated cell into a subject. The ex vivo procedure may be used on autologous or heterologous cells, but is preferably used on autologous cells. In preferred embodiments, the dendritic cells are isolated from peripheral blood or bone marrow, but may be isolated from any source of dendritic cells. When the ex vivo procedure is performed to specifically produce dendritic cells active against a specific cancer or other type of antigen, the dendritic cells may be exposed to the antigen in addition to the CpG and immunopotentiating cytokine. In other cases the dendritic cell may have already been exposed to antigen but may not be expressing the antigen on the surface efficiently. Alternatively the dendritic cell may be exposed to the immunopotentiating cytokine and exposed to the antigen, by either direct contact or exposure in the body and then the dendritic cell is returned to the body followed by administration of CpG directly to the subject, either systemically or locally. Activation will dramatically increase antigen processing. The activated dendritic cell then presents the cancer antigen on its surface. When returned to the subject, the activated dendritic cell expressing the cancer antigen activates T cells in vivo which are specific for the cancer antigen. Ex vivo manipulation of dendritic cells for the purposes of cancer immunotherapy have been described in several references in the art, including Engleman, E. G., 1997, *Cytotechnology*, 25:1; Van Schooten, W., et al., 1997, *Molecular Medicine Today*, June, 255; Steinman, R. M., 1996, *Experimental Hematology*, 24, 849; and Gluckman, J. C., 1997, *Cytokines, Cellular and Molecular Therapy*, 3:187. The ex vivo activation of dendritic cells of the invention may be performed by routine ex vivo manipulation steps known in the art, but with the use of CpG and immunopotentiating cytokine as the activator.

The dendritic cells may also be contacted with CpG and immunopotentiating cytokine using in vivo methods. In order to accomplish this, CpG and immunopotentiating cytokine are administered directly to a subject in need of immunotherapy. The CpG and immunopotentiating cytokine may be administered in combination with an antigen or may be administered alone. In some embodiments, it is preferred that the CpG and immunopotentiating cytokine be administered in the local region of the tumor, which can be accomplished in any way known in the art, e.g., direct injection into the tumor, with implants that release the drug combination, etc.

Dendritic cells useful according to the invention may be isolated from any source as long as the cell is capable of being activated by CpG and cytokine to produce an active antigen expressing dendritic cell. Several in vivo sources of immature dendritic cells may be used according to the methods of the invention. For instance bone marrow dendritic cells and peripheral blood dendritic cells are both excellent sources of immature dendritic cells that are activated by CpG and cytokine. Other sources may easily be determined by those of skill in the art without requiring undue experimentation, by for instance, isolating a primary source of dendritic cells and testing activation by CpG in vitro. The invention also encompasses the use of any immature dendritic cells maintained in culture as a cell line as long as the cell is capable of being activated by CpG and cytokine. Such cell types may be routinely identified using standard assays known in the art.

Peripheral blood dendritic cells isolated by immunomagnetic cell sorting, which are activated by CpG and cytokine, represent a more physiologic cell population of dendritic cells than monocyte derived dendritic cells. Immature dendritic cells comprise approximately 1–3% of the cells in the bone marrow and approximately 10–100 fold less in the peripheral blood. Peripheral blood cells can be collected using devices well-known in the art, e.g., haemonetics model v. 50 apheresis device (Haemonetics, Braintree, Mass.). Red blood cells and neutrophils are removed from the blood by centrifugation. The mononuclear cells located at the interface are isolated. Methods for isolating CD4+ dendritic cells from peripheral blood have been described O'Doherty U., et al. *J. Exp. Med.* 1993; 178: 1067–1076. In the presence of GM-CSF alone these cells differentiate to dendritic cells with characteristic cellular processes within two days. Differentiation is accompanied by an increase in cell size, granularity and MHC II expression, which can be easily followed using flow cytometry. Freshly isolated dendritic cells cultured in the absence of GM-CSF rapidly undergo apoptosis. Strikingly, in the presence of CpG oligonucleotides without addition of GM-CSF, both cell survival and differentiation is markedly improved compared to GM-CSF. In the presence of CpG, dendritic cells form cell clusters which when examined by ultrastructural techniques such as electron microscopy revealed characteristic dense multilamellar intracytoplasmic bodies and multi-vesicular structures, which were not present in dendritic cells incubated with GM-CSF. Scanning electron microscopy showed long veil and sheet-like processes thought to be used for intercellular interactions, and an irregular cell shape. In contrast, cells incubated with GM-CSF were round-shaped and had only minor cellular processes. In addition to promoting survival and differentiation of dendritic cells, a single addition of CpG oligonucleotide led to activation as represented by upregulation of the co-stimulatory molecules ICAM-1 (CD54), B7-2 (CD86) and CD40. The combination of CpG oligonucleotide and GM-CSF enhanced the expression of CD86 and CD40 synergistically, proving that activation is not due to CpG-induced GM-CSF.

Method for Making Immunostimulatory Nucleic Acids

For use in the instant invention, nucleic acids can be synthesized de novo using any of a number of procedures well known in the art. For example, the b-cyanoethyl phosphoramidite method (S. L. Beaucage and M. H. Caruthers, 1981, *Tet. Let.* 22:1859); nucleoside H-phosphonate method (Garegg, et al., 1986, *Tet. Let.* 27:4051–4051; Froehler, et al., 1986, *Nucl. Acid. Res.* 14:5399–5407; Garegg, et al., 1986, *Tet. Let.* 27:4055–4058, Gaffney, et al., 1988), *Tet. Let.* 29:2619–2622. These chemistries can be performed by a variety of automated oligonucleotide synthesizers available in the market. Alternatively, oligonucleotides can be prepared from existing nucleic acid sequences (e.g. genomic or cDNA) using known techniques, such as those employing restriction enzymes, exonucleases or endonucleases.

For use in vivo, nucleic acids are preferably relatively resistant to degradation (e.g. via endo- and exo-nucleases). Secondary structures, such as stem loops, can stabilize nucleic acids against degradation. Alternatively, nucleic acid stabilization can be accomplished via phosphate backbone modifications as discussed above. A preferred stabilized nucleic acid can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made for example as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A., 1990, *Chem. Rev.* 90:544; Goodchild, J., 1990, *Bioconjugate Chem.* 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C.

For administration in vivo, nucleic acids and cytokines may be associated with a molecule that results in higher affinity binding to target cell (e.g. dendritic cell) surfaces and/or increased cellular uptake by target cells to form a "nucleic acid/cytokine delivery complex" as discussed above. Nucleic acids can be ionically, or covalently associated with appropriate molecules using techniques which are well known in the art. A variety of coupling or crosslinking agents can be used, for example protein A, carbodiimide, and N-succinimidyl-3-(2-pyridyldithio) propionate (SPDP). Nucleic acids can alternatively be encapsulated in liposomes or virosomes using well-known techniques.

The compositions of the invention, including activated dendritic cells, isolated CpG nucleic acid molecules, cytokines, and mixtures thereof are administered in pharmaceutically acceptable compositions. When administered, the compositions of the invention are applied in pharmaceutically-acceptable amounts. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. As used herein, a composition of a CpG oligonucleotide and/or an immuno-potentiating cytokine means the compounds described above as well as salts thereof.

The compositions of the invention may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the compositions of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend of course, upon the particular composition selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The compositions may conveniently be presented in unit dosage form and may be prepared by any of the methods well-known in the art of pharmacy. All methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration may be presented as discrete units, such as capsules, tablets, lozenges, each containing a predetermined amount of the compositions of the invention. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compositions of the invention is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854, 480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

EXAMPLES

Example 1

Materials and Methods

Tumor Model and Tumor Antigens

The 38C13 murine B cell lymphoma model has been used extensively in studies of antibody-based therapy and active immunization of lymphoma (Kwak, L. W., et al., *Proc. Natl. Acad. Sci. USA* 93:10972–7, 1996). The idiotype (Id) of the 38C13 surface IgM serves as a highly specific tumor-associated antigen (Bergman, Y., and Haimovich, J., *Eur. J. Immunol.* 7:413–7, 1977). Id was obtained from the supernatant of a cell line that secretes 38C13 IgM as described (Eshhar, Z., et al., *J. Immunol.* 122:2430, 1979), and purified by protein a affinity chromatography. Purified Id was conjugated to keyhole limpet hemocyanin (KLH) using glutaraldehyde and used as the immunogen. The cell line that produces 38C13 Id/murine GM-CSF fusion protein was kindly provided by Dr. Ronald Levy. This cell line was cultured in a hollow fiber reactor (Unisyn Technologies, Hopkinton, Mass.), and fusion protein obtained by protein a affinity chromatography. The fusion protein consists of the 38C13 Id heavy and light chain variable regions, the human $IgG_1$ heavy and light chain constant regions, and murine GM-CSF sequences (Tao, M. H., and Levy, R., *Nature* 362:755–758, 1993). Bifunctional reactivity was confirmed by ELISA prior to use. Plates were coated with anti-Id, serial dilutions of fusion protein added, and the presence of bound GM-CSF moieties assessed by probing with anti-GM-CSF antibodies. 38C13 Id/human GM-CSF fusion protein was obtained in a similar manner and used as a control.

Immunization

Two phosphorothioate CpG oligonucleotides were purchased commercially and produced under GMP conditions (Oligos Etc., Wilsonville, Oreg.). Both oligonucleotide sequences had similar effects in all assays. CpG oligonucleotide 1758 was used unless stated otherwise. Oligonucleotide 1758 had the sequence

TCTCCCAGCGTGCGCCAT (SEQ ID NO: 104)

and oligonucleotide 1826 had the sequence

TCCATGACGTTCCTGACGTT (SEQ ID NO:3)

Both CpG oligonucleotide were unmethylated. No detectable endotoxin was present in either CpG oligonucleotide by LAL assay. Prior studies demonstrated non-immunostimulatory oligonucleotide had little adjuvant effect (Weiner, G. J., et al., *Proc. Natl. Acad. Sci. USA* 94:10833–10837, 1997), therefore non-immunostimulatory oligonucleotide were not included in the current studies. Murine GM-CSF for in vitro production of dendritic cells it was purchased commercially (PeproTech, Rocky Hill, N.J.). GM-CSF for in vivo studies was kindly supplied by Immunex (Seattle, Wash.).

Female C3H/HeN mice, obtained from Harlan-Sprague-Dawley, were housed in the University of Iowa Animal Care Unit and used at 6–9 weeks of age. Each mouse was immunized subcutaneously with indicated antigen and adjuvant in a total volume of 200 $\mu$l using PBS as a vehicle.

ELISA Determination of Anti-Id Levels

Serum was obtained by retroorbital puncture from mice following inhalation anesthesia with metophane. Microtiter plates were coated with 5 $\mu$g/ml 38C13 IgM or irrelevant IgM overnight. IgM-coated plates were blocked with 5% milk, and serial dilutions of serum were added. Serum from naive mice to which a known concentration of monoclonal anti-Id was added served as a standard. Plates were washed, and heavy chain-specific goat anti-mouse IgG, $IgG_1$, or $IgG_{2a}$ (Southern Biotechnology Associates, Birmingham, Ala.) added following by the colorimetric substrate p-nitrophenylphosphate. Plates were evaluated using a microplate reader. Test curves were compared with standard curves to determine the concentration of anti-Id. Values were considered valid only if the standard curves and the sample curves had the same shape. Reactivity of serum with a control, irrelevant murine IgM was evaluated in parallel and was negative in all assays, confirming the immune response was not due to development of an isotypic response.

In Vivo Survival Studies

Three days after a single subcutaneous immunization using the indicated antigen and adjuvant, mice were inoculated i.p. with 1,000 viable 38C13 cells. Cells were growing in log phase for at least 4 days prior to inoculation. Mice that developed tumor displayed inguinal and abdominal masses, ascites, and cachexia. All mice that developed tumor died. Survival was determined, and significance with respect to time to death was assessed using Cox regression analysis. For statistical purposes, survival of 60 days was assigned for mice that remained tumor free. All such mice remained tumor free indefinitely, and were monitored for a minimum of 100 days.

Dendritic Cell Production and Stimulation

Dendritic cells were obtained using a modification of the approach previously described (Zitvogel, L., et al., *J. Ex. Med.* 183:87–97, 1996; Mayordomo, J. I., et al., *Nature Medicine* 1:1297–302, 1995). Briefly, bone marrow cells were obtained by flushing the femurs and tibias of naive 6–8 week old C3H/HeN mice. Red blood cells were lysed and T-cells removed by complement-mediated lysis using a mixture of anti-CD3 (145.2C11), anti-CD4 (GK1.5) and anti-CD8 (53.6.7) antibodies. B-cells were then removed by panning using a flask coated with anti-B220. Remaining cells were allowed to adhere overnight. Nonadherent cells were cultured in media supplemented with 1000 U/ml GM-CSF and 1000 U/ml muIL-4 (PeproTech, Rocky Hill, N.J.) at a concentration of $1.25 \times 10^5$ cells/ml. Media was changed after 4 days, and dendritic cells harvested 7 days after bone marrow harvest. Dendritic cell phenotype and morphology were confirmed by flow cytometric analysis and scanning electron microscopy. Dendritic cells were washed, counted, and $1 \times 10^5$ were cultured for 18 hours in a total volume of 200 $\mu$l with antigen at a final concentration of 100 $\mu$g/ml and CpG oligonucleotide at a final concentration of 50 $\mu$g/ml. For measurement of cytokine levels, all samples were run in quadruplicate. Supernatant was harvested and assayed by ELISA for the presence of IL-6 and IL-12 as described (Klinman, D. M., et al., *Proc. Natl. Acad. Sci. USA* 93:2879–83, 1996; Yi, A. K., et al., *J. Immunol.* 156:558–64, 1996).

Example 2

Figure 1:
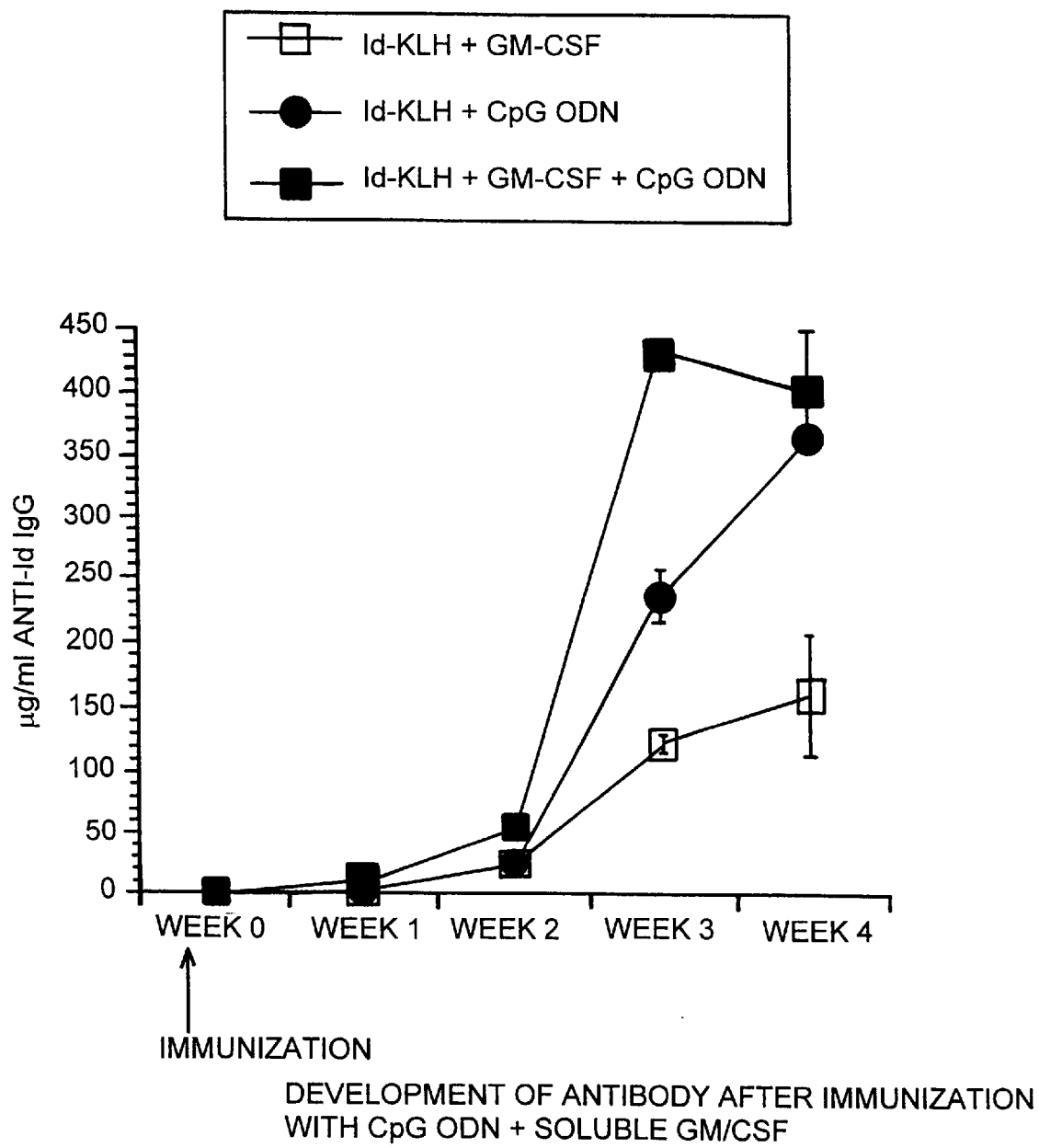
FIG. 1 is a graph showing the production of anti-Id IgG following immunization using a combination of CpG ODN and soluble GM-CSF. Mice were immunized with 50 μg of Id-KLH as a single subcutaneous dose mixed in aqueous solution with GM-CSF, CpG ODN or both. Blood was obtained weekly, and serum was evaluated for the presence of anti-Id IgG by ELISA. Normal mouse serum supplemented with a known concentration of monoclonal anti-Id was used as a standard. Three mice were included in each group.

CpG Oligonucleotide Enhances Development of an Antibody Response to Id-KLH Immunization When Using GM-CSF as an Adjuvant CpG oligonucleotide is known to induce production by APCs of a number of cytokines including GM-CSF (Krieg, A. M., *Trends in Microbiology* 4:73–6, 1996). In order to determine if the addition of CpG oligonucleotide to GM-CSF would further enhance the immune response mice were immunized with a single subcutaneous injection of 50 $\mu$g of Id-KLH in PBS mixed in aqueous solution with 50 $\mu$g of CpG oligonucleotide, 10 $\mu$g of GM-CSF, or a combination of CpG oligonucleotide and GM-CSF. Serum was obtained weekly and evaluated by ELISA for the presence of antigen-specific IgG (anti-Id IgG). As illustrated in FIG. 1, mice immunized using both CpG oligonucleotide and GM-CSF developed the highest levels of anti-Id IgG. The effect of these two adjuvants appeared to be additive.

The combination of GM-CSF and CpG oligonucleotide could therefore enhance a number of different steps in the induction of the immune response with GM-CSF increasing antigen uptake while CpG oligonucleotide enhances the downstream response including production of cytokines involved in effector cell activation. In addition, CpG oligonucleotide contributes by synergistically promoting B-cell activation through the antigen receptor, and so preferentially activating antigen-specific B-cells (Krieg, A. M., et al.,

*Nature* 374:546–9, 1995). The data presented above indicate immunization strategies involving the combination of GM-CSF and CpG oligonucleotide are particularly effective. CpG oligonucleotide and soluble GM-CSF were only additive in their ability to induce anti-IdIgG after immunization with Id-KLH which may have been due to the short half life of murine GM-CSF (Kedar, E., et al., *J. Immunotherapy* 20:180–93, 1997).

Example 3

Figure 2:
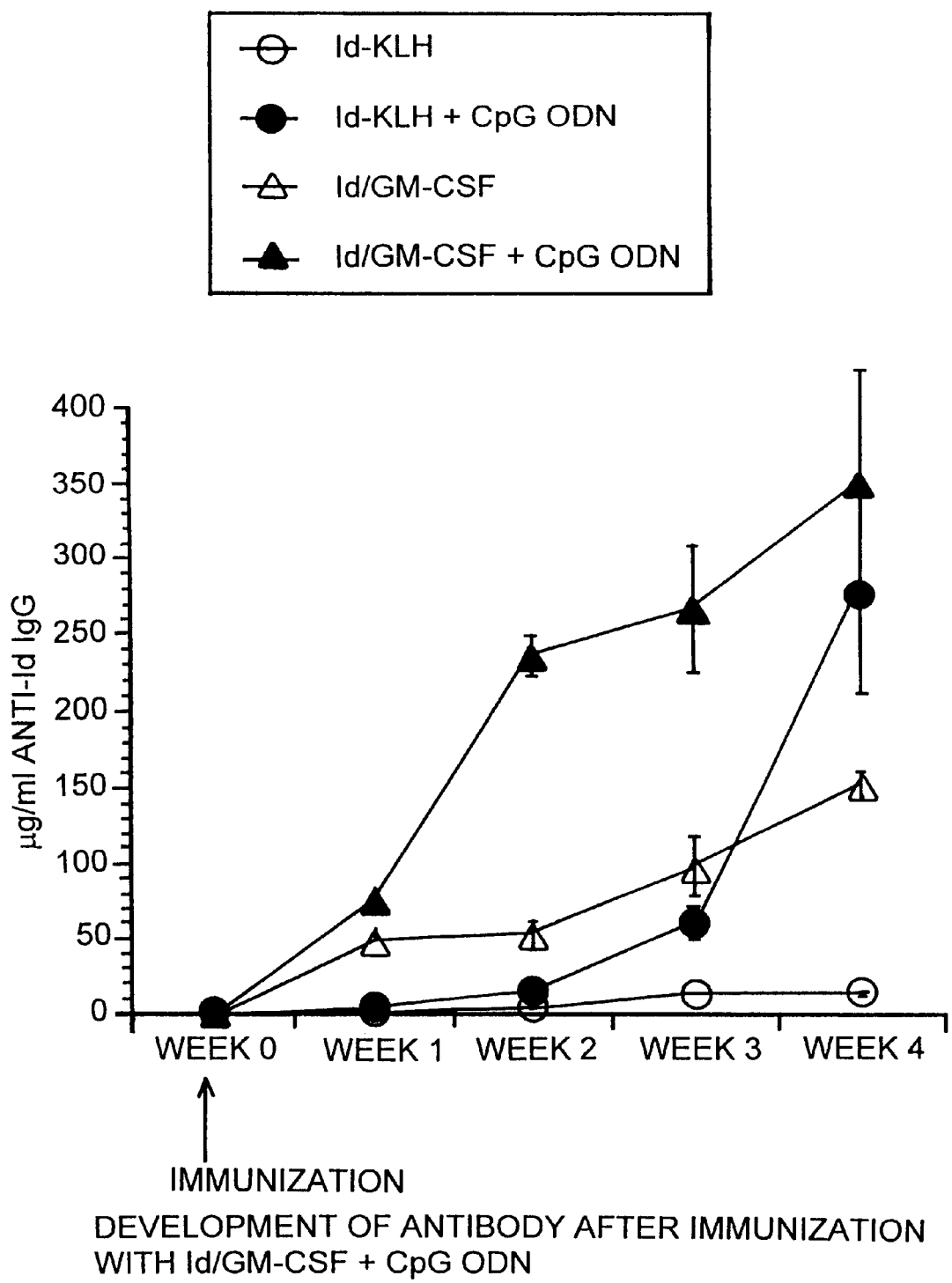
FIG. 2 is a graph showing that immunization using a combination of Id/GM-CSF fusion protein and CpG ODN enhances production of antigen-specific IgG. Mice were immunized with 50 μg of Id/GM-CSF as a single subcutaneous dose with or without CpG ODN. Blood was obtained weekly, and serum was evaluated for the presence of anti-Id IgG by ELISA. Normal mouse serum supplemented with a known concentration of monoclonal anti-Id was used as a standard. Three mice were included in each group.

CpG Oligonucleotide Enhances Production of Anti-Id Antibodies Following Immunization with Id/GM-CSF Fusion Protein The Id/GM-CSF fusion protein consisting of the 38C13 variable regions, human IgG constant regions, and murine GM-CSF (Id/GM-CSF) has been shown to be an excellent immunogen (Tao, M. H., and Levy, R., *Nature* 362:755–758, 1993). In order to evaluate if CpG oligonucleotide can further enhance the specific antibody response induced by Id/GM-CSF, mice were immunized with Id-KLH or Id/GM-CSF with and without CpG oligonucleotide as an adjuvant. Serum was obtained weekly and anti-Id IgG levels determined. No toxicity was observed in any mice. As illustrated in FIG. 2, CpG oligonucleotide enhanced production of anti-Id antibodies in response to Id/GM-CSF.

In a separate experiment, mice were immunized on day 0 and boosted on day 14 with the same antigen and adjuvant. The combination of Id/GM-CSF and CpG oligonucleotide induced remarkably high levels of anti-Id IgG after two immunizations (FIG. 3). Serum obtained 1 week after the final immunization contained over 2.5 mg/ml anti-Id IgG. A fusion protein consisting of 38C13 Id and human GM-CSF (Id/human GM-CSF) was included as a control since human GM-CSF is not active in the murine system. Id/human GM-CSF was identical to Id/GM-CSF, except the murine GM-CSF sequences were replaced with human GM-CSF sequences. Levels of anti-Id produced after immunization using Id/human GM-CSF with or without CpG oligonucleotide were significantly lower than those seen following Id/GM-CSF and similar to those seen with Id-KLH, demonstrating that biologically active GM-CSF was important for the observed effects.

Example 4

Figure 4:
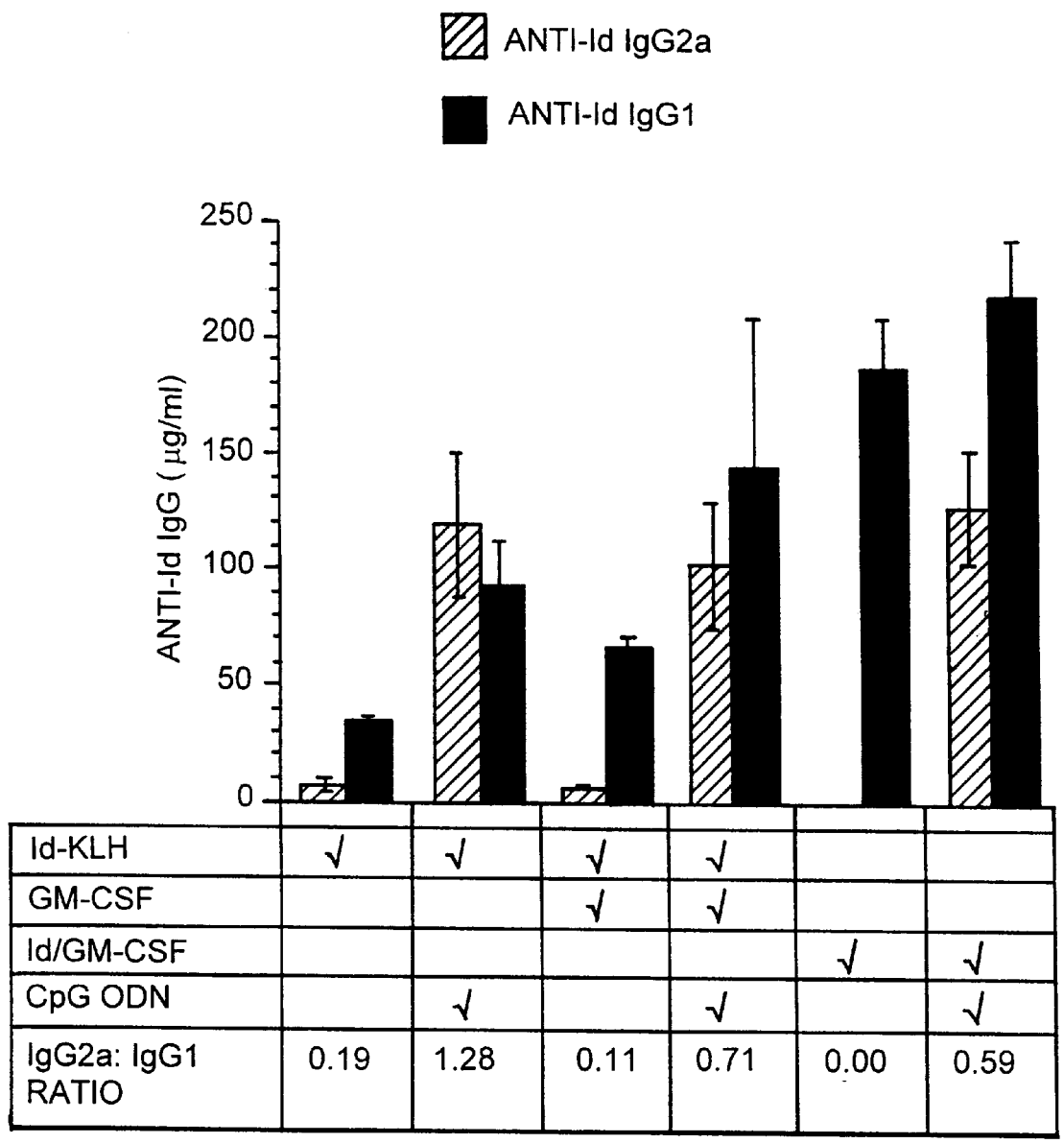
FIG. 4 is a bar graph showing that CpG ODN enhances production of antigen specific antibody of $IgG_{2a}$ isotype. Mice were immunized with a single dose using various combinations of Id-KLH, GM-CSF, Id/GM-CSF fusion protein, and CpG ODN. Serum was obtained 4 weeks after a single immunization. Anti-d $IgG_1$ and $IgG_{2a}$ was determined by ELISA. Three mice were included in each group.

CpG Oligonucleotide Enhances Production of Antigen Specific Antibody of $IgG_{2a}$ Isotype Enhanced production of $IgG_1$ reflects a Th2 response, whereas predominant $IgG_{2a}$ production indicates a Th1 response (Stevens, T. L., et al., *Nature* 334:255–8, 1988). Moreover, murine $IgG_{2a}$ is more effective than murine IgG at mediating antibody-dependent cellular cytotoxicity, and monoclonal $IgG_{2a}$ works better than monoclonal IgG with the identical variable region as a set of therapeutic antibodies for treating tumors in mice (Kaminski, M. S.,*J. Immunol.* 136:1123–1130, 1986). An isotype was performed analysis on anti-Id IgG, and the presence of anti-Id $IgG_1$ and $IgG_{2a}$ was assessed following immunization (FIG. 4). Immunization included various combinations of Id-KLH or Id/GM-CSF with GM-CSF or CpG oligonucleotide. Serum was sampled 4 weeks after a single immunization. CpG oligonucleotide induced enhanced production of anti-Id $IgG_{2a}$ compared with that seen under the corresponding conditions without CpG oligonucleotide. Similar $IgG_1/IgG_{2a}$ ratios were seen at other time points.

Example 5

Figure 5:
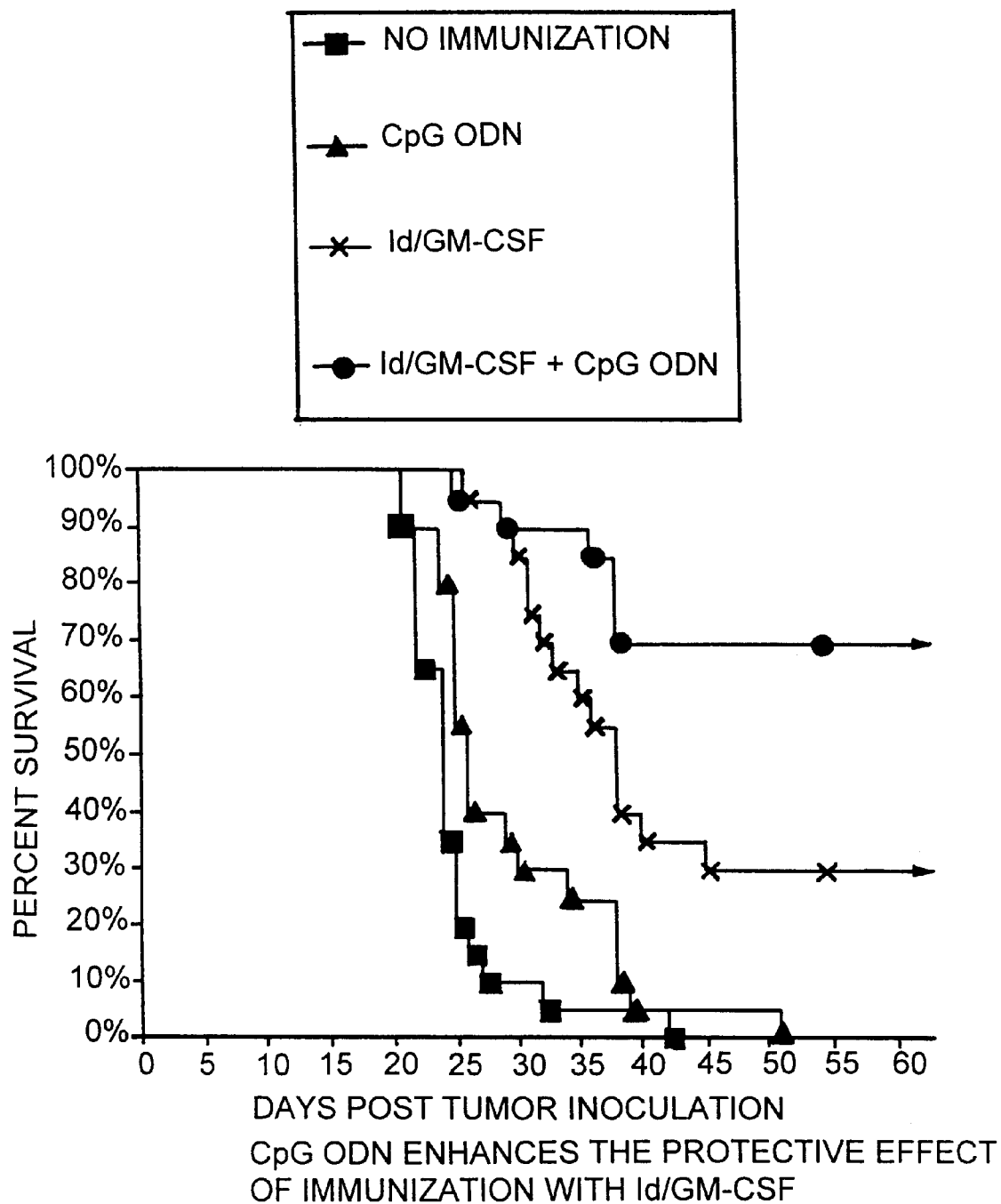
FIG. 5 is a survival curve showing that CpG ODN enhances the protective effect of Id/GM-CSF protection against tumor growth. Mice were immunized with a single injection of Id/GM-CSF and/or CpG ODN and challenged with tumor 3 days later. Survival was followed for 100 days. All mice that were alive after 51 days remained tumor-free for the entire observation period. Twenty mice were included in each group.

Immunization Using CpG Oligonucleotide and ID/GM-CSF Fusion Protein Further Protection of Mice From Tumor Growth In order to evaluate whether CpG oligonucleotide can also serve as an effective adjuvant with Id/GM-CSF immunization, mice were challenged with tumor three days after a single immunization with Id/GM-CSF with or without CpG oligonucleotide. Immunization using this schedule was only minimally effective with Id-KLH. CpG oligonucleotide 1758 and CpG oligonucleotide 1826 were equally effective at prolonging survival when used alone or in combination with Id/GM-CSF. The data illustrated in FIG. 5 represents the combined results of mice treated with CpG oligonucleotide 1758 and CpG oligonucleotide 1826. All unimmunized mice, and mice treated with CpG oligonucleotide without antigen, developed tumor and died within 50 days. Thirty percent of mice immunized with I/GM-CSF alone remained disease free, whereas 70% of the group immunized with Id/GM-CSF and CpG oligonucleotide remained disease free. Mice immunized with Id/GM-CSF and CpG oligonucleotide had survival that was statistically superior to that seen with no immunization or treatment with CpG oligonucleotide alone (P<0.001). The difference between those immunized with Id/GM-CSF alone versus those immunized with CpG oligonucleotide plus Id/GM-CSF approached statistical significance (P–0.072).

In these studies and in the studies of Example 5, remarkable levels of anti-Id IgG were achieved after repeated immunization with Id/GM-CSF and CpG oligonucleotide. CpG oligonucleotide shifted the response to a $IgG_{sa}$ under all conditions studied including immunization with soluble GM-CSF and the Id/GM-CSF fusion protein, suggesting an enhanced Th1 response. Immunization using this approach translated into protection from tumor growth only 3 days after immunization with Id/GM-CSF and CpG oligonucleotide. This is the most effective protection reported to date in this extensively studied model.

Example 6

CpG Oligonucleotide Effects on Dendritic Cell Phenotype

Figure 6:
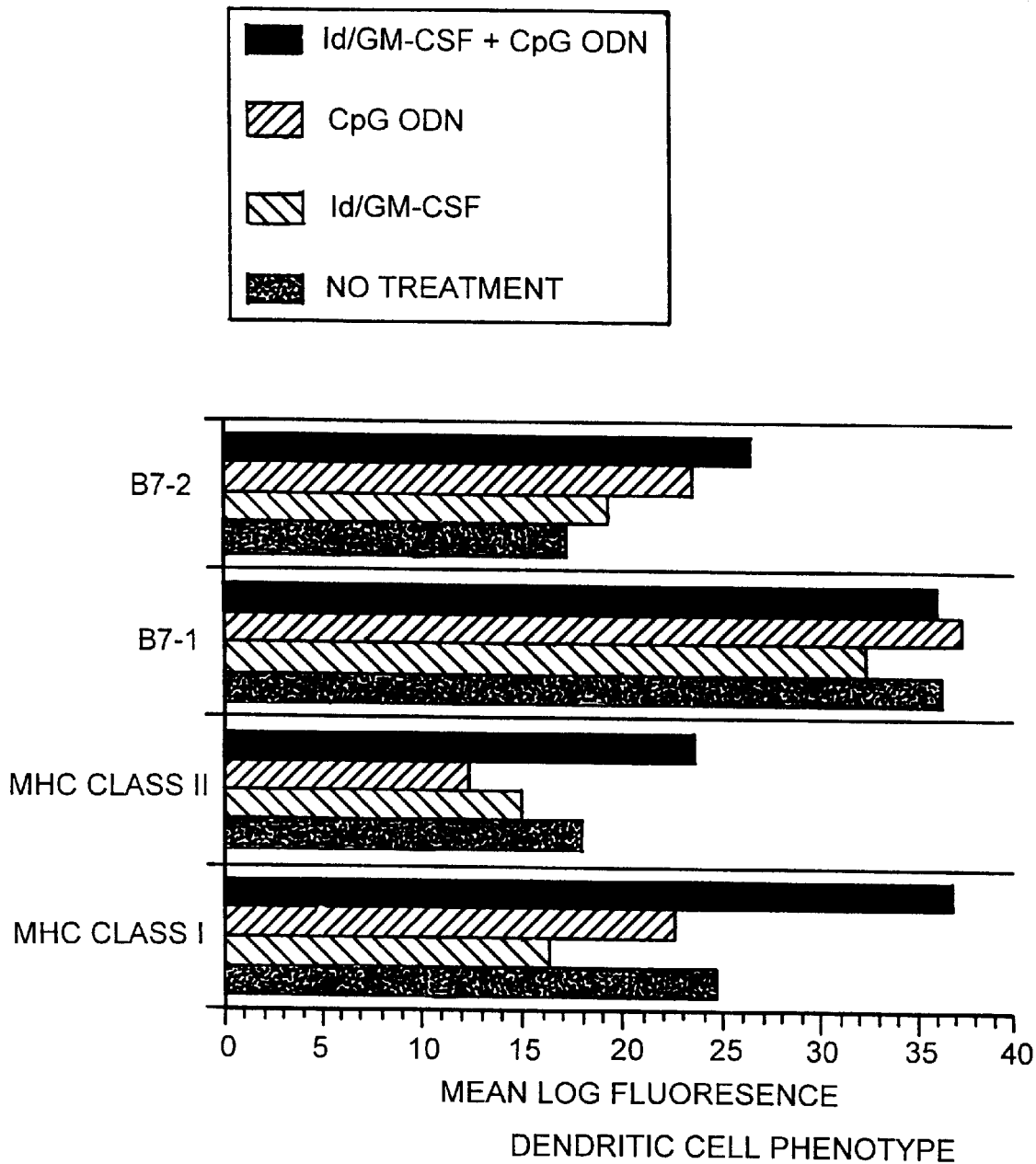
FIG. 6 is a bar graph showing the expression of MHC class I, MHC class II, CD80, and CD86 after pulsing of bone marrow-derived dendritic cells with Id/GM-CSF and/or CpG ODN.

The synergistic effects of CpG oligonucleotide and GM-CSF suggested the possibility that these agents together may enhance expression of costimulatory molecules or MHC by APCs. The expression of these molecules by bone-marrow derived dendritic cells was evaluated. Flow cytometric analysis of dendritic cells pulsed with Id/GM-CSF and/or CpG oligonucleotide demonstrated a modest increase in expression of class I and class II MHC in response to the combination of Id/GM-CSF and CpG oligonucleotide. Baseline expression of CD80 and CD86 expression was high, and was not altered extensively by Id/GM-CSF or CpG oligonucleotide (FIG. 6).

Example 7

CpG Oligonucleotide Enhances Production of IL-12 By Dendritic Cells Pulsed With Id/GM-CSF

Figure 7:
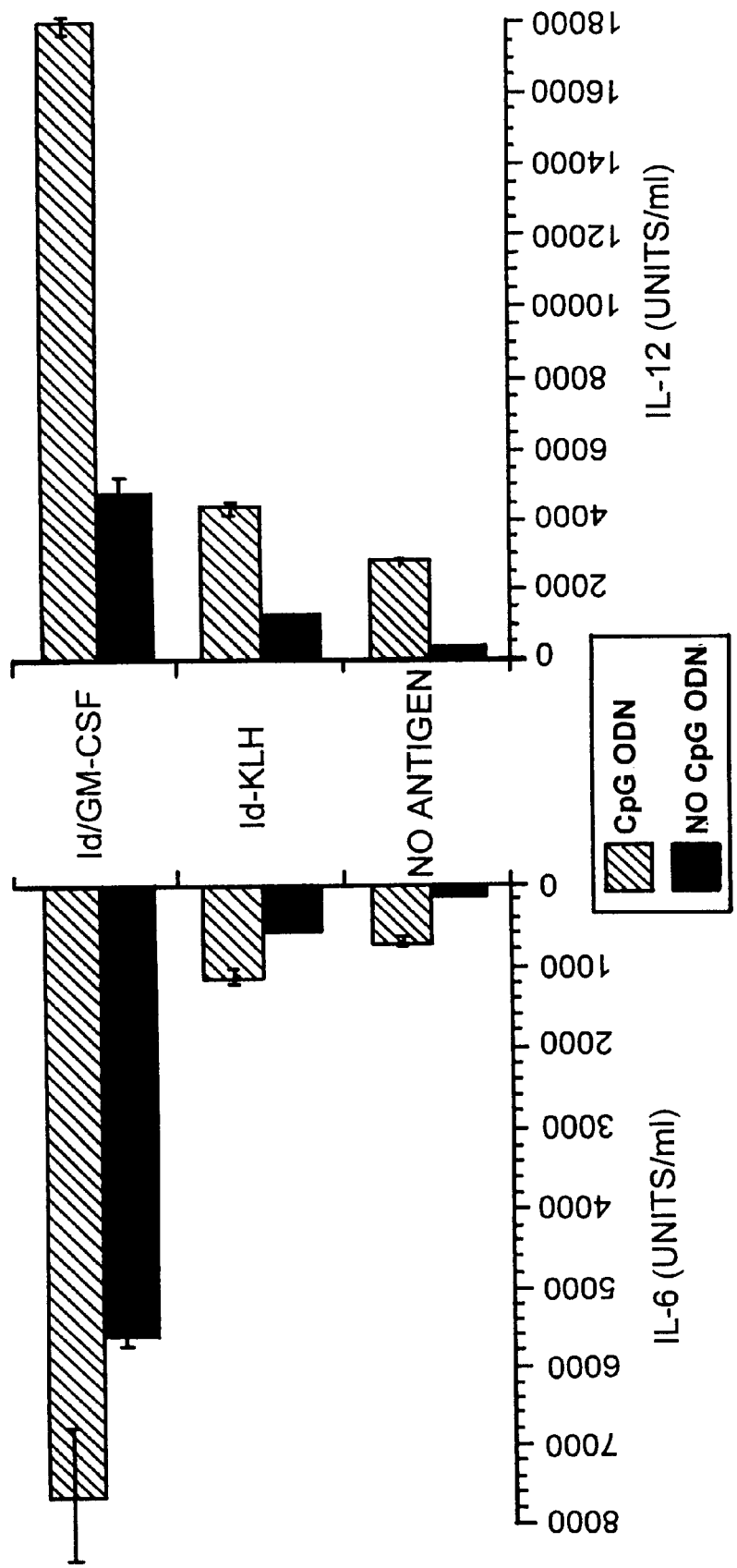
FIG. 7 is a bar graph illustrating that CpG ODN enhances production IL-12 by dendritic cells pulsed with Id-KLH or Id/GM-CSF. Bone marrow derived dendritic cells were pulsed with antigen with and without CpG ODN for 18 hours, and production of IL-12 and IL-6 determined by ELISA. CpG ODN markedly enhanced production of IL-12 by dendritic cells, particularly those pulsed with the Id/GM-CSF fusion protein.

The enhanced Th1 response to antigen could be explained by the ability of CpG oligonucleotide to enhance production of IL-12 by APCs such as dendritic cells. The production of IL-12 by bone-marrow derived dendritic cells that were pulsed with antigen, including Id/GM-CSF, was assessed in the presence of CpG oligonucleotide. As illustrated in FIG. 7, pulsing of dendritic cells with CpG oligonucleotide increased production of IL-12, particularly when cells were also pulsed with Id/GM-CSF. IL-6 production by dendritic cells was also increased by the addition CpG oligonucleotide to Id/GM-CS, although the effect was less pronounced than for IL-12. The impact of GM-CSF alone on dendritic cell production of cytokines was not studied since these cells were generated using GM-CSF. The markedly enhanced production of IL-12 by dendritic cells induced by CpG oligonucleotide may at least in part explain the enhanced Th1 response.

Example 8

Identification of Phosphorothioate Oligonucleotide That Induce Human IL-12 Secretion

The ability of a CpG oligonucleotide to induce IL-12 secretion is a good measure of its adjuvant potential, especially in terms of its ability to induce a Th1 immune response, which is highly dependent on IL-12. Therefore, the ability of a panel of phosphorothioate oligonucleotide to induce IL-12 secretion from human PBMC in vitro (Table 1) was examined. These experiments showed that in some human PBMC, most CpG oligonucleotide could induce IL-12 secretion (e.g., expt. 1). However, other donors responded to just a few CpG oligonucleotide (e.g., expt. 2). Oligonucleotide 2006 was a consistent inducer of IL12 secretion from most subjects (Table 2).

TABLE 2

Induction of human IL-12 secretion by Phosphorothioate CpG oligonucleotide

| ODN[1] | sequence (5'-3') | | IL-12 (pg/ml) expt. 1 | expt. 2 |
|---|---|---|---|---|
| None | | | 0 | 0 |
| 1962 | TCCTGTCGTTCCTTGTCGTT | (SEQ. ID NO:79) | 19 | 0 |
| 1965 | TCCTGTCGTTTTTGTCGTT | (SEQ. ID NO:81) | 36 | 0 |
| 1967 | TCGTCGCTGTCTGCCCTTCTT | (SEQ. ID NO:82) | 41 | 0 |
| 1968 | TCGTCGCTGTTGTCGTTTCTT | (SEQ. ID NO:83) | 24 | 0 |
| 2005 | TCGTCGTTGTCGTTGTCGTT | (SEQ. ID NO:89) | 25 | 0 |
| 2006 | TCGTCGTTTTGTCGTTTTGTCGTT | (SEQ ID NO: 90) | 29 | 15 |
| 2014 | TGTCGTTGTCGTTGTCGTT | (SEQ. ID NO:96) | 28 | 0 |
| 2015 | TCGTCGTCGTCGTT | (SEQ ID NO:97) | 14 | 0 |
| 2016 | TGTCGTTGTCGTT | (SEQ. ID NO:98) | 3 | 0 |

[1]PBMC were collected from normal donors and spun over Ficoll, then cultured at $10^6$ cells/well in 96 well microtiter plates with or without the indicated oligonucleotide which were added to cultures at µg/ml. Supernatants were collected at 24 hr and tested for IL-12 levels by ELISA as described in methods. A standard curve was run in each experiment, which represents a different donor.

Example 9

CpG and GM-CSF Synergistically Increase Co-Stimulatory Molecules on DC

Methods

Detection of Endotoxin

The activity of LPS is standardized by the FDA using the limulus amebocyte lysate (LAL) assay (EU/ml). The lower detection limit of the LAL-assay in our hands was 0.03 EU/ml (LAL-assay BioWhittaker, Walkersville, Md.). The LPS sample used in our studies (from *salmonella typhimurium*, Sigma Chemical Co., St. Louis, Mo.) had an activity of 4.35 ng/EU. No endotoxin could be detected in the oligonucleotides (<0.075 EU/mg).

Results

Figure 8:
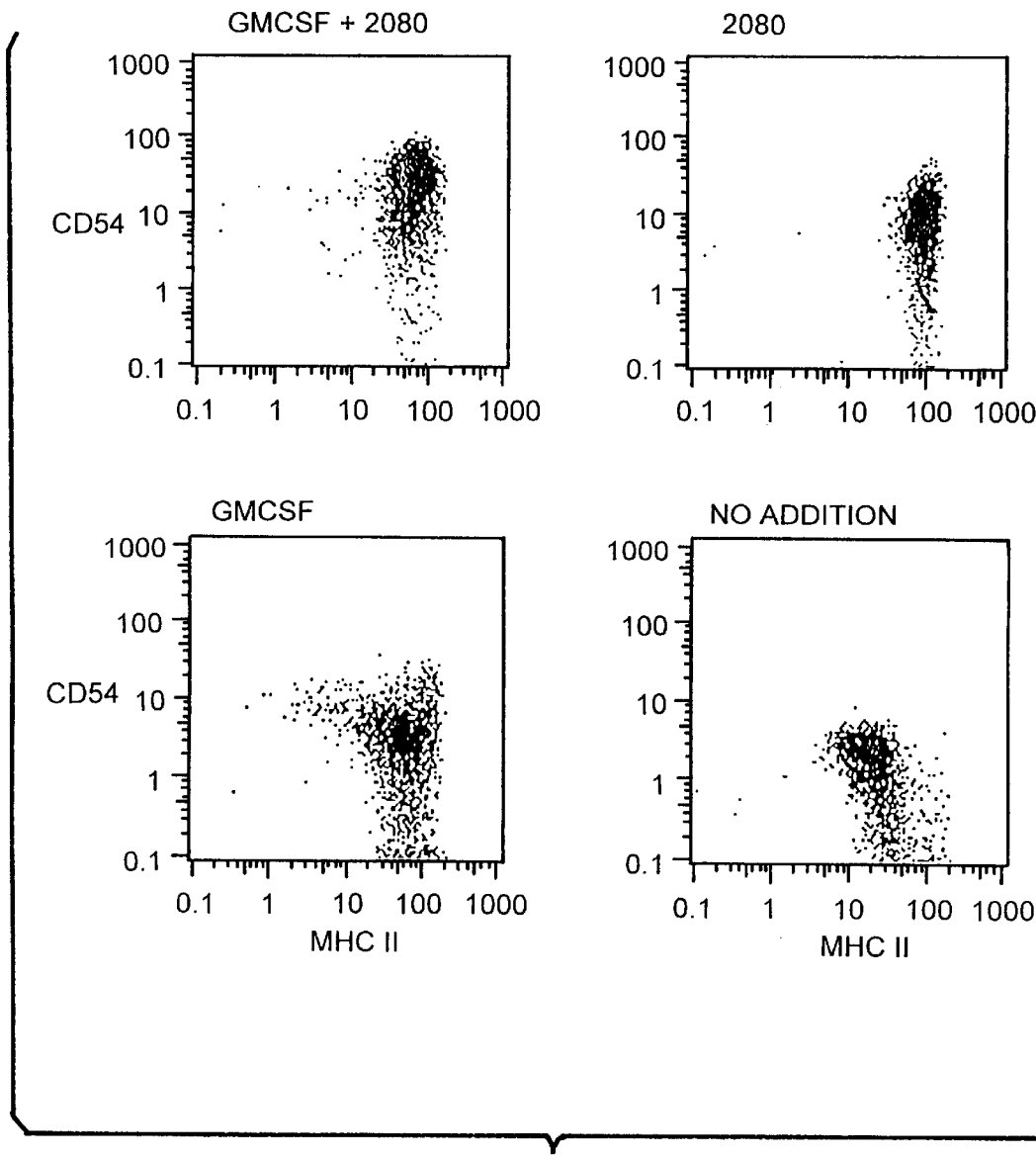
FIG. 8 shows FACS charts demonstrating that ICAM-1 and MHC II expression of dendritic cells in response to GM-CSF and CpG. Dendritic precursor cells were incubated for 48 hours in the presence of GM-CSF (800 U/ml) and 2006 (CpG phosphorothioate; 6 μg/ml). Expression of ICAM-1 (CD54) and MHC II was examined by flow cytometry (2500 viable cells are counted in each sample).

Differentiation of DC by the criteria of morphology and MHC II expression is not sufficient for the induction of a specific immune response by DC. Functional activation of DC requires by the expression of co-stimulatory molecules. We examined the effect of CpG on the expression of the intercellular adhesion molecule-1 (ICAM-1, CD54), and the co-stimulatory surface molecules B7-2 (CD86) and CD40. First, we were interested if an enhanced expression of MHC II on DC (differentiation) was correlated to activation reflected by CD54 expression. No positive correlation could be found confirming that differentiation is not necessarily associated with activation of DC (FIG. 8). The expression of the co-stimulatory molecules CD54 (FIG. 9, panel A), CD86 (FIG. 9, panel B) and CD40 (FIG. 9, panel C) was quantified in flow cytometry by the mean fluorescence intensity (MFI) of viable DC. In all experiments, CpG was superior to GMCSF in enhancing expression of co-stimulatory molecules. Compared to the cells only sample, the CpG oligonucleotide 2006 enhanced the expression of CD54 (25.0+−5.7 vs. 7.0+−1.8; p=0.02, n=5), CD 86 (3.9+−0.8 vs. 1.6+−0.3; p=0.01; n=5) and CD40 (3.5+−1.0 vs. 0.9+−0.1; p=0.04, n=4). The combination of GMCSF and 2006 showed an additive effect for CD54 (38.5+−7.9; p=0.03; n=5), and enhanced the expression of CD86 and CD40 synergistically (CD86: 7.0+−1.6; p=0.01; n=5; CD40: 8.5+−1.0; p<0.01; n=4).

Specificity was tested using 2117 (methylated version of 2006) and 2078 (GpC version of 2080). The non-CpG oligonucleotide 2117 showed no synergistic enhancement of CD40 expression when combined with GMCSF. An assay was performed on primary dendritic cells in which dendritic cells are cultured with the indicated compounds (under the conditions described above). Then we measured the surface expression of Cd86 or CD40 on the dendritic cells, and it's ability to drive T cell proliferation in a allogeneic mixed lymphocyte reaction (indicated as the % of T cells in the culture that proliferate in response to the dendritic cells activation). The results are shown in Table 3.

TABLE 3

| Compound | CD86 (5 Exp) | CD40 (4 Exp.) | T cell proliferation |
|---|---|---|---|
| GM-CSF | 1.9 | 2.5 | 13.3 |
| CpG | 3.9 | 3.5 | 19.7 |
| CpG + GM-CSF | 7.0 | 8.5 | 25.6 |

TABLE 1

| sequences | |
|---|---|
| GCTAGACGTTAGCGT | (SEQ ID NO: 1) |
| GCTAGATGTTAGCGT | (SEQ ID NO: 2) |
| GCTAGAZGTTAGCGT | (SEQ ID NO: 3) |
| GCTAGACGTTAGZGT | (SEQ ID NO: 4) |
| GCATGACGTTAGCT | (SEQ ID NO: 5) |
| ATGGAAGGTCCAGCGTTCTC | (SEQ ID NO: 6) |
| ATCGACTCTCGAGCGTTCTC | (SEQ ID NO: 7) |
| ATZGACTCTZGAGZGTTCTC | (SEQ ID NO: 8) |
| ATZGACTCTCGAGCGTTCTC | (SEQ ID NO: 9) |
| ATCGACTCTCGAGCGTTZTC | (SEQ ID NO: 10) |
| ATCGACTCTCGAACGTTCTC | (SEQ ID NO: 11) |
| GAGAACGCTGGACCTTCCAT | (SEQ ID NO: 12) |
| GAGAACGCTCGACCTTCCAT | (SEQ ID NO: 13) |
| GAGAACGCTCGACCTTCGAT | (SEQ ID NO: 14) |
| GAGCAAGCTGGACCTTCCAT | (SEQ ID NO: 15) |
| GAGCAZGCTGGACCTTCCAT | (SEQ ID NO: 16) |
| GAGAACGCTGGACZTTCCAT | (SEQ ID NO: 17) |
| GAGAACGATGGACCTTCCAT | (SEQ ID NO: 18) |

TABLE 1-continued

| sequences | |
|---|---|
| GAGAACGCTCCAGCACTGAT | (SEQ ID NO: 19) |
| CCATGTCGGTCCTGATGCT | (SEQ ID NO: 20) |
| TCCATGCTGGTCCTGATGCT | (SEQ ID NO: 21) |
| TCCATGTZGGTCCTGATGCT | (SEQ ID NO: 22) |
| TCCATGTCGGTZCTGATGCT | (SEQ ID NO: 23) |
| TCCATGACGTTCCTGATGCT | (SEQ ID NO: 24) |
| TCCATGTCGGTCCTGACGCA | (SEQ ID NO: 25) |
| TCAACGTT | (SEQ ID NO: 26) |
| TCAAGCTT | (SEQ ID NO: 27) |
| TCAGCGCT | (SEQ ID NO: 28) |
| TCTTCGAT | (SEQ ID NO: 29) |
| TCTTCGAA | (SEQ ID NO: 30) |
| CAACGTT | (SEQ ID NO: 31) |
| CCAACGTT | (SEQ ID NO: 32) |
| CAACGTTCT | (SEQ ID NO: 33) |
| TCAACGTC | (SEQ ID NO: 34) |
| ATGGACTCTCCAGCGTTCTC | (SEQ ID NO: 35) |
| ATAGGAGGTCCAACGTTCTC | (SEQ ID NO: 36) |
| ATCGACTCTCGAGCGTTCTC | (SEQ ID NO: 37) |
| ATGGAGGCTCCATCGTTCTC | (SEQ ID NO: 38) |
| ATZGGACTCTZGAGZGTTCTC | (SEQ ID NO: 39) |
| ATCGACTCTCGAGZGTTCTC | (SEQ ID NO: 40) |
| GCATGACGTTGAGCT3' | (SEQ ID NO: 41) |
| TCCATGTCGGTCCTGATGCT | SEQ ID NO: 42 |
| TCCATGCCGGTCCTGATGCT | SEQ ID NO: 43 |
| TCCATGGCGGTCCTGATGCT | SEQ ID NO: 44 |
| TCCATGACGGTCCTGATGCT | SEQ ID NO: 45 |
| TCCATGTCGATCCTGATGCT | SEQ ID NO: 46 |
| TCCATGTCGCTCCTGATGCT | SEQ ID NO: 47 |
| TCCATGTCGTTCCTGATGCT | SEQ ID NO: 48 |
| TCCATAACGTTCCTGATGCT | SEQ ID NO: 49 |
| TCCATGACGTCCCTGATGCT | SEQ ID NO: 50 |
| TCCATCACGTGCCTGATGCT | SEQ ID NO: 51 |
| GGGGTCAACGTTGACGGGG | (SEQ ID NO: 52) |
| GGGGTCAGTCGTGACGGGG | (SEQ ID NO: 53) |
| GCTAGACGTTAGTGT | (SEQ ID NO: 54) |
| GCTAGAZGTTAGTGT | (SEQ ID NO: 55) |
| TCCATGTCGTTCCTGATGCT | (SEQ ID NO: 56) |

TABLE 1-continued sequences

| Sequence | SEQ ID NO |
|---|---|
| TCCATGTZGTTCCTGATGCT | (SEQ ID NO: 57) |
| ACCATGGACGATCTGTTTCCCCTC | (SEQ ID NO: 58) |
| TCTCCCAGCGTGCGCCAT | (SEQ ID NO: 59) |
| TACCGCGTGCGACCCTCT | (SEQ ID NO: 60) |
| ACCATGGACGAACTGTTTCCCCTC | (SEQ ID NO: 61) |
| ACCATGGACGAGCTGTTTCCCCTC | (SEQ ID NO: 62) |
| ACCATGGACGACCTGTTTCCCCTC | (SEQ ID NO: 63) |
| ACCATGGACGTACTGTTTCCCCTC | (SEQ ID NO: 64) |
| ACCATGGACGGTCTGTTTCCCCTC | (SEQ ID NO: 65) |
| ACCATGGACGTTCTGTTTCCCCTC | (SEQ ID NO: 66) |
| CACGTTGAGGGCAT | (SEQ ID NO: 67) |
| CTGCTGAGACTGGAG | (SEQ ID NO: 68) |
| TCAGCGTGCGCC | (SEQ ID NO: 69) |
| ATGACGTTCCTGACGTT | (SEQ ID NO: 70) |
| TCTCCCAGCGGGCGCAT | (SEQ ID NO: 71) |
| TCTCCCAGCGCGCGCCAT | (SEQ ID NO: 72) |
| TCCATGTCGTTCCTGTCGTT | (SEQ ID NO: 73) |
| TCCATAGCGTTCCTAGCGTT | (SEQ ID NO: 74) |
| TCGTCGCTGTCTCCGCTTCTT | (SEQ ID NO: 75) |
| TCCTGACGTTCCTGACGTT | (SEQ ID NO: 76) |
| TCCTGTCGTTCCTGTCGTT | (SEQ ID NO: 77) |
| TCCATGTCGTTTTGTCGTT | (SEQ ID NO: 78) |
| TCCTGTCGTTCCTTGTCGTT | (SEQ ID NO: 79) |
| TCCTTGTCGTTCCTGTCGTT | (SEQ ID NO: 80) |
| TCCTGTCGTTTTTTGTCGTT | (SEQ ID NO: 81) |
| TCGTCGCTGTCTGCCCTTCTT | (SEQ ID NO: 82) |
| TCGTCGCTGTTGTCGTTTCTT | (SEQ ID NO: 83) |
| TCCATGTZGTTCCTGTZGTT | (SEQ ID NO: 84) |
| TCCAGGACTTCTCTCAGGTT | (SEQ ID NO: 85) |
| TCCATGCGTGCGTGCGTTTT | (SEQ ID NO: 86) |
| TCCATGCGTTGCGTTGCGTT | (SEQ ID NO: 87) |
| TCCACGACGTTTTCGACGTT | (SEQ ID NO: 88) |
| TCGTCGTTGTCGTTGTCGTT | (SEQ ID NO: 89) |
| TCGTCGTTTTGTCGTTTTGTCGTT | (SEQ ID NO: 90) |
| TCGTCGTTGTCGTTTTGTCGTT | (SEQ ID NO: 91) |
| GCGTGCGTTGTCGTTGTCGTT | (SEQ ID NO: 92) |
| GCGGCGGGCGGCGCGCGCCC | (SEQ ID NO: 93) |
| TGTCGTTTGTCGTTTGTCGTT | (SEQ ID NO: 94) |
| TGTCGTTGTCGTTGTCGTTGTCGTT | (SEQ ID NO: 95) |
| TGTCGTTGTCGTTGTCGTT | (SEQ ID NO: 96) |
| TCGTCGTCGTCGTT | (SEQ ID NO: 97) |
| TGTCGTTGTCGTT | (SEQ ID NO: 98) |
| TCCATAGCGTTCCTAGCGTT | (SEQ ID NO: 99) |
| TCCATGACGTTCCTGACGTT | (SEQ ID NO: 100) |
| GTCG(T/C)T | (SEQ ID NO: 101) |
| TGTCG(T/C)T | (SEQ ID NO: 102) |
| TCCATGAGCTTCCTGAGTCT | (SEQ ID NO: 103) |
| TCTCCCAGCGTGCGCCAT | (SEQ ID NO: 104) |
| TCCATGACGTTCCTGACGTT | (SEQ ID NO: 105) |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

What is claimed is:

1. A method for stimulating an immune response in a subject, comprising:

administering to a subject exposed to an antigen an effective amount for inducing a synergistic antigen specific immune response of an immunopotentiating cytokine selected from the group consisting of GM-CSF, IL-2, IL-4 and IFN-γ, and an immunostimulatory CpG oligonucleotide having a sequence including at least the following formula:

$$5' \; X_1CGX_2 \; 3'$$

wherein the oligonucleotide includes at least 8 nucleotides wherein C is unmethylated and wherein $X_1$ and $X_2$ are nucleotides, wherein the cytokine is a peptide, whereby an antigen is optionally additionally administered, and wherein the antigen and the CpG oligonucleotide are not conjugated.

2. A The method of claim 1, wherein the immunopotentiating cytokine is an antigen-cytokine fusion protein.

3. The method of claim 2, wherein the antigen-cytokine fusion protein is an antigen-GM-CSF fusion protein.

4. The method of claim 1, wherein the antigen is selected from the group consisting of a tumor antigen, a microbial antigen, and an allergen.

5. The method of claim 4, wherein the antigen is a tumor antigen.

6. The method of claim 1, wherein the antigen is administered to the subject in conjunction with the immunostimulatory CpG oligonucleotide and the immunopotentiating cytokine.

7. The method of claim 1, wherein the subject is passively exposed to the antigen.

8. The method of claim 1, wherein the subject has a neoplastic disorder.

9. The method of claim 1, wherein the subject has a viral infection.

10. The method of claim 1, wherein the subject is a non-human animal.

11. The method of claim 10, wherein the non-human animal is a vertebrate animal selected from the group consisting of a dog, a cat, a horse, a cow, a pig, a sheep, a goat, a chicken, and a primate.

12. A composition, comprising:
an effective amount for synergistically activating a dendritic cell of an immunostimulatory CpG oligonucleotide having a sequence including at least the following formula:

$$5' \; X_1CGX_2 \; 3'$$

wherein the oligonucleotide includes at least 8 nucleotides wherein C is unmethylated and wherein $X_1$ and $X_2$ are nucleotides; and a cytokine selected from the group consisting of GM-CSF, IL-2, IL-4 and IFN-γ, wherein the cytokine is a peptide.

13. The composition of claim 12, wherein the cytokine is GM-CSF.

14. The composition of claim 12, further comprising an antigen and wherein the antigen and the CpG oligonucleotide are not conjugated.

15. The composition of claim 14, wherein the antigen is selected from the group consisting of a cancer antigen, a microbial antigen, and an allergen.

16. A method for activating a dendritic cell, comprising:
contacting a dendritic cell exposed to an antigen with an effective amount for synergistically activating a dendritic cell of an immunopotentiating cytokine selected from the group consisting of GM-CSF, IL-2, IL-4 and IFN-γ, and an immunostimulatory CpG oligonucleotide having a sequence including at least the following formula:

$$5' \; X_1CGX_2 \; 3'$$

wherein the oligonucleotide includes at least 8 nucleotides wherein C is unmethylated and wherein $X_1$ and $X_2$ are nucleotides, wherein the cytokine is a peptide, whereby an antigen is optionally additionally administered, and wherein the antigen and the CpG oligonucleotide are not conjugated.

17. The method of claim 16, wherein the antigen is a tumor antigen.

18. A method for treating a subject having a neoplastic disorder, comprising:
administering to the tumor of a subject having a neoplastic disorder an immunopotentiating cytokine selected from the group consisting of GM-CSF, IL-2, IL-4 and IFN-γ, and an immunostimulatory CpG oligonucleotide having a sequence including at least the following formula:

$$5' \; X_1CGX_2 \; 3'$$

wherein the oligonucleotide includes at least 8 nucleotides wherein C is unmethylated and wherein $X_1$ and $X_2$ are nucleotides, in an amount effective for synergistically increasing survival time of the subject with respect to a subject administered the immunostimulatory CpG oligonucleotide or the immunopotentiating cytokine alone, where the cytokine is a peptide.

19. The method of claim 18, wherein the tumor is selected from the group consisting of a lymphoma and a tumor of the brain, lung, ovary, breast, prostate, colon, and skin.

20. The method of claim 18, wherein the immunostimulatory CpG oligonucleotide and the immunopotentiating cytokine are injected directly into the tumor.

21. The method of claim 18, wherein the subject is a non-human animal.

22. The method of claim 21, wherein the non-human animal is a vertebrate animal selected from the group consisting of a dog, a cat, a horse, a cow, a pig, a sheep, a goat, a chicken, and a primate.

23. The method of claim 22, wherein the tumor is selected from the group consisting of lymphoma an a tumor of the brain, lung, ovary, breast, prostate, colon, and skin.

* * * * *

UNITED STATES PATENT AND TRADEMARK OFFICE
CERTIFICATE OF CORRECTION

PATENT NO. : 6,218,371 B1
DATED : April 17, 2001
INVENTOR(S) : Krieg et al.

It is certified that error appears in the above-identified patent and that said Letters Patent is hereby corrected as shown below:

Column 10,
Line 17, delete "orbiviurses" and insert -- orbiviruses --.

Column 12,
Line 18, delete "NO: 93" and insert -- NO: 100 --.

Column 13,
Place the following words in *italics:* -- Reoviridae, Orthoreovirus, Orbivirus, Rotavirus, Picomaviridae, Enterovirus, Cardiovirus, Rhinovirus , Apthovirus, Calciviridae, Togaviridae, Alphavirus, Flavirus, Rubivirus, Pestivirus, Bunyaviridae, Bunyvirus, Phlebovirus, Nairovirus, Uukuvirus, Orthomyxoviridae, Influenza, paramyxoviridae, Paramyxovirus, Morbillivirus, Pneumovirus --.

Column 13, line 64 through Column 14, line 27,
Delete from "forest" through "mice)".

Column 14,
Place the following words in *italics:* -- Rhabdoviridae, Vesiculovirus, Arenaviridae, Coronaaviridae, Poxviridae, Iridoviridae, Herpesviridae, Adenoviridae, Papoviridae --.

Column 15,
Line 5, delete "Parvoviridae" and insert -- *Parvoviridae* --.

Column 16,
Line 30, delete "Togaviridae" and insert -- *Togaviridae* --.
Line 31, delete "Flaviviridae" and insert -- *Flaviviridae* --.

Column 17,
Line 44, delete "Felidae" and insert -- *Felidae* --.

Column 22,
Line 65, delete ""oligonucleotide" and insert -- oligonucleotide --.

UNITED STATES PATENT AND TRADEMARK OFFICE
CERTIFICATE OF CORRECTION

PATENT NO. : 6,218,371 B1
DATED : April 17, 2001
INVENTOR(S) : Krieg et al.

It is certified that error appears in the above-identified patent and that said Letters Patent is hereby corrected as shown below:

Column 25,
Line 13, delete "TCGTCGTTTTGTCGTTTTGTCGTT (SEQ ID NO:89)" and insert -- GGGGTCAGTCGTGACGGGG (SEQ ID NO: 53) --.
Line 25, delete "TCGTCGTTTTGTCGTTTTGTCGTT (SEQ ID N0:90),".
Line 26, delete "TCGTCGTTGTCGTTTTGTCGTT (SEQ ID N0:91),".
Line 27, delete "TGTCGTTGTCGTTGTCGTT (SEQ ID N0:96),".
Lines 38 and 65, delete "C." and insert -- C --.

Column 30,
Line 5, delete "de novo" and insert -- *de novo* --.
Line 12, delete "1988)" and insert -- 1988 --.
Line 12, delete "29:2619-2622" and insert -- 29:2619-2622) --.

Column 32,
Line 60, delete "Tumor Model and Tumor Antigens" and insert -- Tumor Model and Tumor Antigens --.

Column 33,
Line 20, delete "Immunization" and insert -- Immunization --.
Line 29, delete "(SEQ ID NO:3)" and insert -- (SEQ ID NO:100) --.
Line 37, delete "it".
Line 46, delete "ELISA Determination of Anti-ld Levels" and insert -- ELISA Determination of Anti-Id Levels --.
Line 65, delete "In Vivo Survival Studies" and insert -- In Vivo Survival Studies --.

Column 34,
Line 11, delete "Dendritic Cell Production and Stimulation" and insert -- Dendritic Cell Production and Stimulation --.

Columns 37 and 38,
Table 2, Footnote 1, delete "ug/ml" and insert -- 6ug/ml --.

Column 38,
Line 6, delete "IL_12" and insert -- IL-12 --.
Line 43, delete "Methods" and insert -- Methods --.
Line 53, delete "Results" and insert -- Results --.

UNITED STATES PATENT AND TRADEMARK OFFICE
CERTIFICATE OF CORRECTION

PATENT NO. : 6,218,371 B1
DATED : April 17, 2001
INVENTOR(S) : Krieg et al.

It is certified that error appears in the above-identified patent and that said Letters Patent is hereby corrected as shown below:

<u>Column 39,</u>
Line 21, delete "Cd86" and insert -- CD86 --.

<u>Column 78,</u>
Line 53, delete "an" and insert -- and --.

Signed and Sealed this

Eleventh Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,218,371 B1
APPLICATION NO. : 09/286098
DATED : April 17, 2001
INVENTOR(S) : Krieg et al.

It is certified that error appears in the above-identified patent and that said Letters Patent is hereby corrected as shown below:

OTHER PUBLICATIONS
After "D'Andrea et al." cite insert -- Davis H et al., CpG DNA is a Potent Enhancer of Specific Immunity in Mice Immunized with Recombinant Hepatitis B Surface Antigen. *J. of Immunology*, (1998), 160:2870-76. --

After "Leonard et al." cite insert -- Liu et al., Immunostimulatory CpG Oligodeoxynu-cleotides Enhance the Immune Response to Vaccine Strategies Involving Granulocyte-Macrophage Cology-Stimulating Factor. *Blood*, (1998), 92(10):3730-36. --

After "Roman M et al." cite insert -- Sato et al., Immunostimulatory DNA Sequences Necessary for Effective Intradermal Gene Immunization. *Science*, v.273, pp.352-54, 1996. --

After "Wagner RW" cite insert -- Weiner et al., Immunostimulatory oligodeoxynucleo-tides containing the CpG motif are effective as immune adjuvants in tumor antigen im-munization. *Proc. Natl. Acad. Sci.* (1997), 94:10833-37.--

Column 1, between the "RELATED APPLICATIONS" paragraph and "FIELD OF THE INVENTION" paragraph, insert
-- GOVERNMENT SUPPORT
The invention was developed at least in part using Federal Funding under a grant from the National Institutes of Health under Grant Number CA77764. Accord-ingly, the government may have rights in the invention.--

Column 1, line 67, delete "1996." and insert --1996).--

Column 7, line 52, delete "Others" and insert --Other--.

Column 10, place the following words in *italics*:
"Picornaviridae", "Calciviridae", "Togaviridae", "Flaviridae", "Coronoviridae", "Rhabdoviridae", "Filoviridae", "Paramyxoviridae", "Orthomyxoviridae", "Bungaviridae", "Arena viridae", "Reoviridae", "Birnaviridae", "Hepadnaviridae", "Parvovirida", "Papovaviridae", "Adenoviridae", "Herpesviridae", "Poxviridae", "Iridoviridae", "Pasturella", "Staphylococci", "Streptococcus", "Pseudomonas", "Salmonella", "Mycobacteria sps", "Streptococcus", "Streptococcus", "Campylobacter Sp.", "Enterococcus sp.", "Corynebacterium sp.", "Bacteroides sp.", "Leptospira", "Rickettsia", "Plasmodium"

Column 10, lines 10, 11, delete "Rhabdoviridae (e.g. vesicular stomatitis viruses, rabies virues)"

UNITED STATES PATENT AND TRADEMARK OFFICE
CERTIFICATE OF CORRECTION

PATENT NO.        : 6,218,371 B1
APPLICATION NO. : 09/286098
DATED                : April 17, 2001
INVENTOR(S)       : Krieg et al.

It is certified that error appears in the above-identified patent and that said Letters Patent is hereby corrected as shown below:

Column 10, line 17, delete "orbiviurses" and insert -- orbiviruses --.

Column 12, line 18, delete "NO: 93" and insert --NO: 100--.

Column 13, place the following words in *italics*:
"Reoviridae", "Orthoreovirus", "Orbivirus", "Rotavirus", "Picomaviridae", "Enterovirus", "Cardiovirus", "Rhinovirus", "Apthovirus", "Calciviridae", "Togaviridae", "Alphavirus", "Flavirus", "Rubivirus", "Pestivirus", "Bunyaviridae", "Bunyvirus", "Phlebovirus", "Nairovirus", "Uukuvirus", "Orthomyxoviridae", "Influenza", "paramyxoviridae", "Paramyxovirus", "Morbillivirus", "Pneumovirus".

Column 13, line 64 through Column 14, line 27, delete from "forest" through "mice)".

Column 14, place the following words in *italics*:
"Rhabdoviridae", "Vesiculovirus", "Arenaviridae", "Coronaaviridae", "Poxviridae", "Iridoviridae", "Herpesviridae", "Adenoviridae", "Papoviridae".

Column 15, line 5, delete "Parvoviridae" and insert --*Parvoviridae*--.

Column 16, line 30, delete "Togaviridae" and insert --*Togaviridae*--.

Column 16, line 31, delete "Flaviviridae" and insert --*Flaviviridae*--.

Column 17, line 44, delete "Felidae" and insert --*Felidae*--.

Column 22, line 65, delete ""oligonucleotide" and insert --oligonucleotide--.

Column 25, line 25, delete "TCGTCGTTTTGTCGTTTTGTCGTT (SEQ ID NO:90),".

Column 25, line 26, delete "TCGTCGTTGTCGTTTTGTCGTT (SEQ ID NO:91),".

Column 25, line 27, delete "TGTCGTTGTCGTTGTCGTT (SEQ ID NO:96),".

Column 25, line 38, delete "C." and insert --C--.

Column 25, line 65, delete "C." and insert -- C--.

Column 30, line 5, delete "de novo" and insert --*de novo*--.

Column 30, line 12, delete "1988)" and insert --1988--.

UNITED STATES PATENT AND TRADEMARK OFFICE
CERTIFICATE OF CORRECTION

| | | |
|---|---|---|
| PATENT NO. | : 6,218,371 B1 | Page 3 of 4 |
| APPLICATION NO. | : 09/286098 | |
| DATED | : April 17, 2001 | |
| INVENTOR(S) | : Krieg et al. | |

It is certified that error appears in the above-identified patent and that said Letters Patent is hereby corrected as shown below:

Column 30, line 12, delete "29:2619-2622" and insert "29:2619-2622)".

Column 32, line 60, delete "Tumor Model and Tumor Antigens" and insert --Tumor Model and Tumor Antigens--.

Column 33, line 20, delete "Immunization" and insert --Immunization--.

Column 33, line 29, delete "(SEQ ID NO:3)" and insert --(SEQ ID NO:100)--.

Column 33, line 37, delete "it".

Column 33, line 46, delete "ELISA Determination of Anti-Id Levels" and insert --ELISA Determination of Anti-Id Levels--.

Column 33, line 65, delete "In Vivo Survival Studies" and insert --In Vivo Survival Studies--.

Column 34, line 11, delete "Dendritic Cell Production and Stimulation" and insert --Dendritic Cell Production and Stimulation--.

Column 38, line 6, delete "IL_12" and insert --IL-12--.

Column 37/38, Table 2, Footnote 1, delete "ug/ml" and insert --6ug/ml--.

Column 38, line 43, delete "Methods" and insert --Methods--.

Column 38, line 53, delete "Results" and insert --Results--.

Column 39, line 21, delete "Cd86" and insert --CD86--.

UNITED STATES PATENT AND TRADEMARK OFFICE
CERTIFICATE OF CORRECTION

PATENT NO. : 6,218,371 B1
APPLICATION NO. : 09/286098
DATED : April 17, 2001
INVENTOR(S) : Krieg et al.

It is certified that error appears in the above-identified patent and that said Letters Patent is hereby corrected as shown below:

Column 78, line 53, delete "an" and insert --and--.

Signed and Sealed this

Seventeenth Day of April, 2007

JON W. DUDAS
*Director of the United States Patent and Trademark Office*